United States Patent
Mogna

(10) Patent No.: US 10,028,982 B2
(45) Date of Patent: *Jul. 24, 2018

(54) COMPOSITION COMPRISING N-ACETYLCYSTEINE AND/OR MICROENCAPSULATED GASTROPROTECTED LYSOZYME IN ASSOCIATION WITH PROBIOTIC BACTERIA CAPABLE OF RESTORING THE STOMACH'S OWN BARRIER EFFECT WHICH IS LOST DURING THE PHARMACOLOGICAL TREATMENT OF GASTRIC HYPERACIDITY

(75) Inventor: Giovanni Mogna, Novara (IT)

(73) Assignee: PROBIOTICAL NORTH AMERICA INC., Chicago, IL (US)

( * ) Notice: Subject to any disclaimer, the term of this patent is extended or adjusted under 35 U.S.C. 154(b) by 59 days.

This patent is subject to a terminal disclaimer.

(21) Appl. No.: 14/344,021

(22) PCT Filed: Sep. 10, 2012

(86) PCT No.: PCT/IB2012/001741
§ 371 (c)(1),
(2), (4) Date: May 9, 2014

(87) PCT Pub. No.: WO2013/034974
PCT Pub. Date: Mar. 14, 2013

(65) Prior Publication Data
US 2014/0328932 A1    Nov. 6, 2014

(30) Foreign Application Priority Data
Sep. 9, 2011  (IT) .............................. RM2011A0477

(51) Int. Cl.
| | | |
|---|---|---|
| *A61K 35/747* | (2015.01) | |
| *A61K 35/74* | (2015.01) | |
| *A23L 33/135* | (2016.01) | |
| *C12R 1/225* | (2006.01) | |
| *A61K 35/741* | (2015.01) | |
| *A61K 35/744* | (2015.01) | |
| *A61K 35/745* | (2015.01) | |
| *A61K 31/198* | (2006.01) | |
| *A61K 38/47* | (2006.01) | |
| *A61K 45/06* | (2006.01) | |
| *A23L 33/00* | (2016.01) | |

(52) U.S. Cl.
CPC .......... *A61K 35/747* (2013.01); *A23L 33/135* (2016.08); *A23L 33/40* (2016.08); *A61K 31/198* (2013.01); *A61K 35/74* (2013.01); *A61K 35/741* (2013.01); *A61K 35/744* (2013.01); *A61K 35/745* (2013.01); *A61K 38/47* (2013.01); *A61K 45/06* (2013.01)

(58) Field of Classification Search
None
See application file for complete search history.

(56) References Cited

U.S. PATENT DOCUMENTS

| | | |
|---|---|---|
| 3,819,838 A | 6/1974 | Smith et al. |
| 4,187,321 A | 2/1980 | Mutai et al. |
| 4,332,790 A | 6/1982 | Sozzi et al. |
| 4,670,272 A | 6/1987 | Chen et al. |
| 4,853,211 A | 8/1989 | Kurobe et al. |
| 5,071,976 A | 12/1991 | Stirling |
| 5,466,463 A | 11/1995 | Ford |
| 6,262,019 B1 | 7/2001 | Keller et al. |
| 6,277,370 B1 | 8/2001 | Cavaliere Ved Vesely et al. |
| 8,257,693 B2 | 9/2012 | Ranganathan |
| 9,005,682 B2 | 4/2015 | Sprenger et al. |
| 9,125,768 B2 | 9/2015 | Husmark et al. |
| 2002/0022019 A1 | 2/2002 | Laulund |
| 2002/0044968 A1 | 4/2002 | Van Lengerich |
| 2004/0185032 A1 | 9/2004 | Burrell |
| 2004/0208863 A1 | 10/2004 | Versalovic et al. |
| 2005/0017013 A1 | 1/2005 | Peisach et al. |
| 2005/0031814 A1 | 2/2005 | Dawes |
| 2005/0095232 A1 | 5/2005 | Volkmann |
| 2006/0039973 A1 | 2/2006 | Aldritt et al. |
| 2006/0121571 A1 | 6/2006 | Klaenhammer et al. |
| 2006/0233774 A1 | 10/2006 | Lim et al. |
| 2007/0122397 A1 | 5/2007 | Sanguansri et al. |

(Continued)

FOREIGN PATENT DOCUMENTS

| | | |
|---|---|---|
| CA | 2221426 | 5/1998 |
| CA | 2739345 | 4/2010 |

(Continued)

OTHER PUBLICATIONS

PCT International Search Report and Written Opinion dated Dec. 17, 2012 for PCT/IB2012/001745 filed on Sep. 10, 2012 in the name of Probiotical S.p.A.
PCT International Search Report dated Mar. 29, 2012 for PCT/IB2012/000095 filed on Jan. 24, 2012 in the name of Probiotical S.p.A.
PCT Written Opinion dated Mar. 29, 2012 for PCT/IB2012/000095 filed on Jan. 24, 2012 in the name of Probiotical S.p.A.
PCT International Preliminary Report on Patentability dated Jul. 30, 2013 for PCT/IB2012/000095 filed on Jan. 24, 2012 in the name of Probiotical S.p.A.

(Continued)

*Primary Examiner* — Michelle F. Paguio Frising
(74) *Attorney, Agent, or Firm* — Steinfl + Bruno LLP

(57) ABSTRACT

The present disclosure refers to a composition with N-acetylcysteine and/or lysozyme; or N-acetylcysteine and microencapsulated gastroprotected lysozyme with pro biotic bacteria for use in the pharmacological treatment of gastric hyperacidity. Said composition is capable of restoring the stomach's own barrier effect, which is lost during the pharmacological treatment of gastric hyperacidity, and of minimizing the secondary effects due to said pharmacological treatment.

8 Claims, 2 Drawing Sheets

(56) References Cited

U.S. PATENT DOCUMENTS

| | | | |
|---|---|---|---|
| 2007/0148149 A1 | 6/2007 | Boettner et al. | |
| 2007/0207132 A1 | 9/2007 | Speelmans et al. | |
| 2007/0269515 A1 | 11/2007 | Henriksen et al. | |
| 2008/0175899 A1 | 7/2008 | Ross et al. | |
| 2008/0187628 A1 | 8/2008 | Champion et al. | |
| 2008/0193485 A1 | 8/2008 | Gorbach et al. | |
| 2009/0170185 A1 | 7/2009 | Hayakawa et al. | |
| 2009/0175843 A1 | 7/2009 | Gans | |
| 2009/0252709 A1* | 10/2009 | Nose .................... | A23L 1/3014 424/93.4 |
| 2010/0003369 A1 | 1/2010 | Ter Haar et al. | |
| 2010/0092440 A1 | 4/2010 | Strozzi et al. | |
| 2011/0177198 A1 | 7/2011 | Songisepp et al. | |
| 2011/0178488 A1 | 7/2011 | Balazs | |
| 2012/0195868 A1 | 8/2012 | Lathan et al. | |
| 2014/0072543 A1 | 3/2014 | Mogna | |

FOREIGN PATENT DOCUMENTS

| | | |
|---|---|---|
| CN | 1345589 A | 4/2002 |
| CN | 105163747 A | 12/2015 |
| EA | 11952 B1 | 9/2004 |
| EA | 10981 B1 | 2/2007 |
| EP | 0002692 | 7/1979 |
| EP | 0845350 | 6/1998 |
| EP | 0956858 | 11/1999 |
| EP | 1600060 | 11/2005 |
| EP | 1600061 | 11/2005 |
| EP | 1840205 A1 | 10/2007 |
| EP | 2000530 A1 | 12/2008 |
| EP | 2210505 A1 | 7/2010 |
| EP | 2269465 A1 | 1/2011 |
| EP | 2338976 A1 | 6/2011 |
| EP | 2360237 A1 | 8/2011 |
| EP | 2626076 A1 | 8/2013 |
| JP | 2006-519014 A | 8/2006 |
| JP | 2008-529535 A | 8/2008 |
| JP | 2009-520470 A | 5/2009 |
| JP | 2010-511033 A | 4/2010 |
| JP | 2010-187670 A | 9/2010 |
| JP | 2001-258549 A | 9/2011 |
| JP | 2013009681 A | 1/2013 |
| KZ | 11784 A | 8/2002 |
| KZ | 17967 B | 6/2011 |
| RU | 2150268 C1 | 6/2000 |
| RU | 2203946 C1 | 5/2003 |
| RU | 2338511 C2 | 11/2008 |
| WO | 94/12142 A1 | 6/1994 |
| WO | 1994/012142 | 6/1994 |
| WO | 97/29762 A1 | 8/1997 |
| WO | 99/49877 | 10/1999 |
| WO | 00/72855 | 12/2000 |
| WO | 2003/090546 A1 | 11/2003 |
| WO | 2004/089278 | 10/2004 |
| WO | 2004/089278 A2 | 10/2004 |
| WO | 2004/101770 | 11/2004 |
| WO | 2006/013588 A1 | 2/2006 |
| WO | 2006/073329 A1 | 7/2006 |
| WO | 2007/029773 A1 | 3/2007 |
| WO | 2007/100765 | 9/2007 |
| WO | 2007/100765 A2 | 9/2007 |
| WO | 2007/125558 | 11/2007 |
| WO | 2008/038075 | 4/2008 |
| WO | 2008/065492 | 6/2008 |
| WO | 2008/153377 A1 | 12/2008 |
| WO | 2009/138218 | 11/2009 |
| WO | 2010/023248 A1 | 3/2010 |
| WO | 2010/099824 | 9/2010 |
| WO | 2010/099824 A1 | 9/2010 |
| WO | 2010/103374 | 9/2010 |
| WO | 2010/133761 A1 | 11/2010 |
| WO | 2010/136891 A1 | 12/2010 |
| WO | 2011/012932 | 2/2011 |
| WO | 2011/017040 | 2/2011 |
| WO | 2011/110918 A1 | 9/2011 |
| WO | 2012/001440 | 1/2012 |
| WO | 2012/101500 A1 | 8/2012 |
| WO | 2013/034974 | 3/2013 |
| WO | 2013/034975 A1 | 3/2013 |
| WO | 2013/050831 A1 | 4/2013 |

OTHER PUBLICATIONS

International Search Report dated Dec. 3, 2012 for International patent application PCT/2012/001848 filed on Sep. 21, 2012.
International Written Opinion dated Dec. 3, 2012 for International patent application PCT/2012/001848 filed on Sep. 21, 2012.
PCT International Search Report dated Sep. 21, 2012 for PCT/IB2012/000895 filed on May 9, 2013 in the name of Probiotical S.P.A.
PCT Written Opinion dated Sep. 21, 2012 for PCT/IB2012/000895 filed on May 9, 2013 in the name of Probiotical S.P.A.
PCT International Preliminary Report on Patentability dated Nov. 12, 2013 for PCT/IB2012/000895 filed on May 9, 2013 in the name of Probiotical S.P.A.
PCT International Search Report dated Aug. 24, 2012 for PCT/IB2012/000897 filed on May 9, 2013 in the name of Probiotical S.P.A.
PCT Written Opinion dated Aug. 24, 2012 for PCT/IB2012/000897 filed on May 9, 2013 in the name of Probiotical S.P.A.
PCT International Preliminary Report on Patentability dated Nov. 12, 2013 for PCT/IB2012/000897 filed on May 9, 2013 in the name of Probiotical S.P.A.
PCT International Search Report dated Sep. 27, 2012 for PCT/IB2012/000907 filed on May 9, 2012 in the name of Probiotical S.P.A.
PCT Written Opinion dated Sep. 27, 2012 for PCT/IB2012/000907 filed on May 9, 2012 in the name of Probiotical S.P.A.
PCT International Preliminary Report on Patentability dated Nov. 12, 2013 for PCT/IB2012/000907 filed on May 9, 2012 in the name of Probiotical S.P.A.
PCT International Search Report dated Dec. 16, 2011for PCT/IB2011/000561 filed on Mar. 17, 2011 in the name of Probiotical S.P.A.
PCT Written Opinion dated Dec. 16, 2011for PCT/IB2011/000561 filed on Mar. 17, 2011 in the name of Probiotical S.P.A.
PCT International Preliminary Report on Patentability dated Sep. 17, 2013 for PCT/IB2011/000561 filed on Mar. 17, 2011 in the name of Probiotical S.P.A.
Italian Search Report dated Nov. 11, 2011 for MI20110792 filed on May 9, 2011 in the name of Probiotical S.P.A.
Written Opinion dated Nov. 11, 2011 for MI20110792 filed on May 9, 2011 in the name of Probiotical S.P.A.
Restriction Requirement dated Jan. 7, 2014 for U.S. Appl. No. 14/005,821, filed Nov. 6, 2013.
Non-Final Office Action dated Jun. 5, 2014 for U.S. Appl. No. 14/005,821, filed Nov. 6, 2013.
A. Amaretti, et al. "Antioxidant properties of potentially probiotic bacteria: in vitro and in vivo activities", Applied Microbiology and Biotechnology. vol. 97 (2), 2013, pp. 809-817.
M. Candela, et al. "Interaction of probiotic Lactobacillus and Bifidobacteriun strains with human intestinal epithelial cells: Adhesion properties, competition against enteropahtogens and modulation of IL-8 production", International Journal of Food Microbiology, vol. 125 (3), pp. 286-292, Jul. 2008.
C P Champagne, et al: "The determination of viable counts in probiotic cultures microencapsulated by spray-coating", Food Microbiology, Academic Press Ltd, London, GB, vol. 27, No. 8, Dec. 1, 2010 (Dec. 1, 2010), pp. 1104-1111. Abstract Only.
Cheikhyoussef, et al. "Antimicrobial activity and partial characterization of bacteriocin-like inhibitory substances (BLIS) produced by Bifidobacterium infantis BCRC 14602", Food Control, Butterworth, London, GB, vol. 20 (6), pp. 553-559, Jun. 2009.
M C Collado, et al: "Probiotic Strains and Their Combination Inhibit In Vitro Adhesion of Pathogens to Pig Intestinal Mucosa", Current Microbiology, Springer-Verlag, NE, vol. 55, No. 3, Jul. 25, 2007 (Jul. 25, 2007), pp. 260-265. Abstract Only.

(56) References Cited

OTHER PUBLICATIONS

M. Del Piano, et al. "Evaluation of the intestinal colonization by microencapsulated probiotic bacteria in comparison with the same uncoated strains", Journal of Clinical Gastroenterology, vol. 44, pp. S42-S46, Sep. 2010.

K. A. Eaton, et al: "Probiotic Lactobacillus reuteri Ameliorates Disease Due to Enterohemorrhagic *Escherichia coli* in Germfree Mice", Infection and Immunity, vol. 79, No. 1, Oct. 25, 2010 (Oct. 25, 2010), pp. 185-191.

M.F. Fernandez, et al: "Probiotic properties of human lactobacilli strains to be used in the gastrointestinal tract", Journal of Applied Microbiology, Oxford, GB, vol. 94, No. 3, Jan. 1, 2003 (Jan. 1, 2003), pp. 449-455.

FAO/WHO. *Guidelines for the Evaluation of Probiotics in Food.* Apr. 30/May 1, 2002, 11 pgs.

M Gueimonde, et al: "Adhesion and competitive inhibition and displacement of human enteropathogens by selected lactobacilli", Food Research International, Elsevier Applied Science, Barking, GB, vol. 39, No. 4, May 1, 2006 (May 1, 2006), pp. 467-471. Abstract Only.

P Hütt, et al: "Antagonistic activity of probioitic lactobacilli and bifidobacteria aganst entero- and uropathogensal model", Journal of Applied Microbiology, vol. 100, No. 6, Jun. 2006 (Jun. 2006), pp. 1324-1332.

K. C. Johnson-Henry, et al: "Lactobacillus rhamnosus Strain GG Prevents Enterohemorrhagic *Escherichia coli* 0157:H7-Induced Changes in Epithelial Barrier Function", Infection and Immunity, vol. 76, No. 4, Apr. 1, 2008 (Apr. 1, 2008), pp. 1340-1348.

J. Kim, et al. "Antimicrobial effect of Bifidobacterium breve and Bifidobacterium infantis against *Salmonella typhimurium* KCTC 1925 and *E.coli* 0157:H7 ATCC 43895", Food Science and Biotechnology, Korean Society of Food Science and Technology, vol. 11 (1), pp. 89-92, Jan. 2002.

Likotrafiti, et al. "Molecular Identification and Anti-pathogenic Activities of Putative Probiotic Bacteria Isolated from Faeces of Healthy Elderly Individuals", Microbial Ecology in Health and Disease, 16, pp. 105-112 (2004).

Meei-Yn Lin, et al., "Axtioxidative effect of intestinal bacteria Bifidobacterium longum ATCC 15708 and Lactobacillus acidophilus ATCC 4356", Digestive Diseases & Sciences 2000, 45: 1617-1622.

Meei-Yn. Lin, et al., "Inhibition of lipid peroxidation by Lactobacillus acidophilus and Bifidobacterium longum", J. Agricultural & Food Chemistry 1999, 47: 3661-3664.

M.A. Losada, et al. "Towards a healthier diet for the colon: the influence of fructooligosaccharides and lactobacilli on intestinal health", Nutrition Research, vol. 22, Jan. 2002, pp. 71-84.

F. Lutgendorff, et al., "Probiotics enhance pancreatic glutathione biosynthesis and reduce oxidative stress in experimental acute pancreatitis", Am. J. Physiol. Gastrointest. Liver Physiol., 2008, vol. 295; G1111-G1121.

M. Malecka, "Antioxidant properties of the unsaponifiable matter isolated from tomato seeds, oat grains and wheat germ oil" Food Chemistry, 2002, vol. 79, pp. 327-330.

A Marchese: "Effect of fosfomycin alone and in combination with N-acetylcysteine on *E. coli* biofilms", International Journal of Antimicrobial Agents, vol. 22, Oct. 1, 2003, Suppl. 2, (Oct. 1, 2003), pp. 95-100. Abstract Only.

Lynne V McFarland: "Meta-analysis of probiotics for the prevention of antibiotic associated diarrhea and the treatment of Clostridium difficile disease", The American Journal of Gastroenterology Apr. 2006 LNKD—PUBMED:16635227, vol. 101, No. 4, Apr. 2006 (Apr. 2006), pp. 812-822.

M. Modesto, et al. "Resistant to freezing and freeze-drying storage processes of potential probiotic bifidobacteria", Annals of Microbiology, 54 (1), pp. 43-48 (2004).

L. Peran, et al., A comparative study of the preventative effects exerted by three probiotics, Bifidobacterium lactis, Lactobacillus casei and Lactobacillus acidophilus, in the TNBS model of rat colitis, J. Applied Microbiology 2007, 103: 836-844.

V Rada, et al: "Susceptibility of bifidobacteria to lysozyme as a possible selection criterion for probiotic bifidobacterial strains", Biotechnology Letters, Springer Netherlands, Dordrecht, vol. 32, No. 3, Nov. 27, 2009 (Nov. 27, 2009), pp. 451-455. Abstract Only.

V. Rada, et al. "Susceptibility of bifidobacteria to nisin", Letters in Applied Microbiology, vol. 26, 1998, pp. 123-125.

S. Torriani, et al. "Differentiation of Lactobacillus plantarum, L. pentosus, and L. paraplantarum by recA Gene Sequence Analysis and Multiplex PCR Assay with recA Gene-Derived Primers", Appl. Environ. Microbiol. 2001. vol. 67 (8), pp. 3450-3454.

J. Walter, et al. "Detection and Identification of Gastrointestinal *Lactobacillus* Species by Using Denaturing Gradient Gel Electrophoresis and Species-Specific PCR Primers", Appl. Environ. Microbiol. 2000. vol. 66 (1), pp. 297-303.

Dan Yang Ying, et al: "Microencapsulated Lactobacillus rhamnosus GG Powders: Relationship of Powder Physical Properties to Probiotic Survival during Storage", Journal of Food Science, vol. 75, No. 9, Nov. 1, 2010 (Nov. 1, 2010), pp. E588-E595. Abstract Only.

S. Zanoni, et al., Growth kinetics on oligo- and polysaccharides and promising features of three antioxidative potential probiotic strains, J. Applied Microbiology 2008, 105: 1266-1276.

L. Zhang, et al., "Evaluation of Lactobacillus rhamnosus GG using an *Escherichia coli* K88 model of piglet diarrhea: Effects on diarrhea incidence, faecal microflora and immune responses", Veterinary Microbiology, Elsevier BV. NL, vol. 141, No. 1-2, Feb. 24, 2010, pp. 142-148. Epub Sep. 11, 2009. Abstract Only.

Hong Lu et al., "New development in the mechanistic understanding of peptic ulcer diseases", Drug Discover Today: Disease Mechanisms, Elsevier, 2006, vol. 3, No. 4, pp. 431-437.

Hien Quoc Huynh et al., "N-Acetylcysteine, a Novel Treatment for *Helicobacter pylori* Infection", Digestive Diseases and Sciences, 2004, vol. 49, Nos. 11/12, pp. 1853-1861.

M. Gotteland, et al., "Systematic review: Are probiotics useful in controlling gastric colonization by *Helicobacter pylori*?", Alimentary Pharmacology & Therapeutics, Blackwell Scientific Publications Ltd., 2006, vol. 23, No. 8, pp. 1077-1086.

Mario Del Piano, et al., "Is microencapsulation the future of probiotic preparations? The increased efficacy of gastro-protected probiotics", Gut Microbes, 2011, vol. 2, No. 2, pp. 120-123.

PCT International Search Report of the International Searching Authority dated Dec. 3, 2012 for Application No. PCT/IB2012/001741 filed on Sep. 10, 2012 in the name of Giovanni Mogna.

PCT Written Opinion of the International Searching Authority dated Dec. 3, 2012 for Application No. PCT/IB2012/001741 filed on Sep. 10, 2012 in the name of Giovanni Mogna.

"7th Probiotics & Prebiotics—new food", Universita Urbaniana, Rome. Poster 66: "Effectiveness of the Two Microorganisms L. Fermentum LF15 and L. Plantarum LP01, Formulated in Slow Release Vaginal Tablets, in Women Affected by Bacterial Vaginosis (BV): A Pilot Study", Sep. 2013. 52 pages.

"Sachet" Webpage from merriam-webster.com, Oct. 7, 2011, accessed via WayBackMachine.com. 1 page.

Alam, M. et al. "Development and Evaluation of Acid-buffering Bioadhesive Vaginal Tablet for Mixed Vaginal Infections" AAPS PharmSciTech 2007; vol. 8, No. 4, Article 109. pp. E1-E8.

Al-Wahsh, I. et al. "Acute probiotic ingestion reduces gastrointestinal oxalate absorption in healthy subjects." Urological Research, vol. 40(3), pp. 191-196. Aug. 2011.

Bordoni, A. et al. "Cholesterol-lowering probiotics: in vitro selection and in vivo testing of bifidobacteria" Applied Microbiology and Biotechnology. Sep. 2013. vol. 97, No. 18 pp. 8273-8281.

Briczinski, E. et al. "Strain-Specific Genotyping of *Bifidobacterium animalis* subsp. *lactis* by Using Single-Nucleotide Polymorphisms, Insertions, and Deletions" Applied and Environmental Microbiology. Dec. 2009. vol. 75, No. 23, pp. 7501-7508.

Castro-Leyva, V. et al. "Preserved Ex Vivo Inflammatory Status in Decidual Cells from Women with Preterm Labor and Subclinical Intrauterine Infection." PLOS ONE, vol. 7 (8), e43605, pp. 1-6. Aug. 2012.

Chilean First Examination report dated Feb. 12, 2016 for Chilean application No. 2013-002148 filed on Jul. 26, 2013 in the name of Probiotical S.P.A., 21 pgs. Spanish with English translation.

(56) References Cited

OTHER PUBLICATIONS

European Commission—Health & Consumer Protection Directorate-General, "Opinion of the Scientific Committee on Animal Nutrition on the Criteria for Assessing the Safety of Micro-Organisms Resistant to Antibiotics of Human Clinical and Veterinary Importance", 2002, pp. 1-20.
European Patent Office Communication pursuant to Article 94(3) EPC in relation to Application No. 12 780 278.3-1401, dated Jun. 12, 2015 4 pages.
First Examination Report dated Apr. 28, 2014 for NZ IP No. 614002 filed on Aug. 6, 2013 in the name of Probiotical S.P.A. 2 pgs.
First Office Action for Chinese Patent Application No. 201280015994.3 dated Mar. 25, 2016. 23 pages. (Chinese original + English translation).
First Office Action for Chinese Patent Application No. 201280022854.9 dated Nov. 4, 2014. 15 pages (Chinese original + English translation).
Grill et al. "Bile salt toxicity to some bifidobacteria strains: Role of conjugated bile salt hydrolase and pH" Canadian Journal of Microbiology. Oct. 2000, 46, pp. 878-884.
Grimoud et al., "In vitro screening of probiotic lactic acid bacteria and prebiotic glucooligosaccharides to select effective synbiotics." Anaerobe 16: 493-500 (2010).
Guo, X. "Basics and Application of Probiotics" Science and Technology Press, 1st Version, Oct. 2002. 2 pages (Chinese Original. English Translation in NPL Reference No. 42).
Hoesl, C. E. et al. "The Probiotic Approach: An Alternative Treatment Option in Urology" European Urology, vol. 47, No. 3, pp. 288-296. Mar. 2005.
Breach Action Filed by the General Secretary of the Andean Community Against the Republic of Peru, Process 89-AI-2000 (Gaceta Oficial, del Acuerdo de Cartagena, Sumario, Tribunal de Justicia de la Comunidad Andina), Ano XVIII, Numero 722, Lima, Oct. 12, 2001, 44 pgs. Spanish with English Abstract.
http://www.ub.es/legmh/capitols/sunyenegre.pdf Dr. Jose Ma Sune Negre, New Galenic Formulations to Forms of Administration (Nuevas Aportaciones Galenicas a las Formas de Administracion. En: Curos de formacion continuada para farmaceuticos de hospital. Fundacion Promocion Medica. Barcelona, 2002, 3, pp. 27-65), 3.2. 27 pgs. Spanish with English Abstract.
Japanese Patent Office Official Action for Japanese Patent Application No. 2013-550962. dated Dec. 1, 2015. 10 pages. (Japanese original + English translation).
Klaver et al. "The Assumed assimilation of cholesterol by lactobacilli and *Bifidobacterium bifidum* is due to their bile salt-deconjugating activity" Appl Environ Microbiology, 1993, vol. 59, No. 4, pp. 1120-1124.
Mei, X. et al. "Manual of New Drug and Special Drug" Technology Press, 2nd Version, Jan. 2001. 3 pages (Chinese Original. English Translation in NPL Reference No. 42).
Milani, C. et al., "Comparative Genomics of *Bifidobacterium animalis* subsp. *lactis* Reveals a Strict Monophyletic Bifidobacterial Taxon", Applied and Environmental Microbiology, 79 (14), 2013, 4304-4315.
Office Action for Russian Patent Application No. 2013137656/15(056766) filed Jan. 24, 2012 on behalf of Probiotical S.P.A. dated Mar. 18, 2016. 10 pages (Russian original + English translation).
Office Action for KZ Application No. 2013/1615.1 filed on Jan. 24, 2012 by Tagbergenova Alma Taishevna et al. dated Jul. 15, 2014. 5 pgs.
Okombo et al., "Probiotic-induced reduction of gastrointestinal oxalate absorption in healthy subjects." Urol. Res. 38: pp. 169-178 (2010).
Opposition filed to Application No. SP-2013-12844. 14 pages. Spanish original with English Translation; Date of Notification: Nov. 17, 2015.
Opposition to Ecuadorian Patent Application SP-2013-13082 on behalf of ALAFAR. 14 pages (Spanish original + English translation). 2015.

Ouoba, L. et al., "Resistance of potential probiotic lactic acid bacteria and bifidobacteria of African and European origin to antimicrobials: Determination and transferability of the resistance genes to other bacteria", International Journal of Food Microbiology, 2008, 121, 217-224.
Ouwehand, A. et al. "Probiotics: an Overview of beneficial effects" Antonie van Leeuwenhoek. 2002, vol. 82; pp. 279-289.
Pascual, L. et al. "Vaginal Colonization and Activity of the Probiotic Bacterium *Lactobacillus fermentum* L23 in a Murine Model of Vaginal Tract Infection", Journal of Medical Microbiology, vol. 59, No. 3, pp. 360-364, Nov. 2009.
PCT International Preliminary Report on Patentability for PCT/IB2012/001745 filed on Sep. 10, 2012 in the name of Probiotical North America Inc. dated Mar. 12, 2014 8 pages.
PCT International Preliminary Report on Patentability issued for International Application No. PCT/IB2014/000739 filed on May 14, 2014 in the name of Probiotical S.P.A. dated Nov. 26, 2015. 14 pages.
PCT International Preliminary Report on Patentability dated Sep. 17, 2013 for PCT/IB2011/000561 filed on Mar. 17, 2011 in the name of Probiotical S.P.A. 6 pgs.
PCT International Search Report issued for PCT/IB2014/000731 filed on May 14, 2014 in the name of Probiotical S.P.A. dated Jul. 25, 2014 7 pages.
PCT International Search Report issued for PCT/IB2014/000739 filed on May 14, 2014 in the name of Probiotical S.P.A. dated Jul. 31, 2014 8 pages.
PCT International Search Report dated Aug. 24, 2012 for PCT/IB2012/000897 filed on May 9, 2013 in the name of Probiotical S.P.A. 4 pgs.
PCT Written Opinion issued for PCT/IB2014/000731 filed on May 14, 2014 in the name of Probiotical S.P.A. dated Jul. 25, 2014 10 pages.
PCT Written Opinion issued for PCT/IB2014/000739 filed on May 14, 2014 in the name of Probiotical S.P.A. dated Jul. 31, 2014 11 pages.
Puccio, G. et al. "Clinical evaluation of a new starter formula for infants containing live *Bifidobacterium longum* BL999 and prebiotics" Nutrition 2007 vol. 23; pp. 1-8.
S. De Keersmaecker et al. "Strong antimicrobial activity of *Lactobacillus rhamnosus* GG against *Salmonella typhimurium* is due to accumulation of lactic acid" Federation of European Microbiological Societies Microbiology Letters 259. (2006) 89-96.
Saggioro, A. "Probiotics in the Treatment of Irritable Bowel Syndrome." Journal of Clinical Gastroenterology, vol. 38(6), pp. S104-S106. Jul. 2004.
Santini, C. et al., "Characterization of probiotic strains: an application as feed additives in poultry against *Campylobacter jejuni*", Int J Food Microbiol., 2010, 141 Suppl 1:S98-108. Epub Apr. 8, 2010. Abstract Only.
Strus, M. et al. "Studies on the Effects of Pro Biotic *Lactobacillus* Mixture Given Orally on Vaginal and Rectal Colonization and on Parameters of Vaginal Health in Women with Intermediate Vaginal Flora" Eurpoean Journal of Obstetrics Gynecology and Reproductive Biology, vol. 163, No. 2 pp. 210-215. Aug. 2012.
The EFSA Journal, "Opinion of the Scientific Panel on Additives and Products or Substances used in Animal Feed on the updating of the criteria used in the assessment of bacteria for resistance to antibiotics of human and veterinary importance", 2005, 223, pp. 1-12.
Vicariotto, F. et al: "65: Effectiveness Of An Association Of A Cranberry Dried Extract, D-Mannose And The Three Microorganisms L. Plantarum Lp01, L. Paracasei, Lpc09 And S. Thermophilus St10 In Women Affected By Cystitis: A Pilot Study", 7th Probiotics & Prebiotics New Foods, pp. 1-52, Jul. 2013.
Wikipedia "Pharmaceutical Drug" Updated Apr. 15, 2016. Downloaded from the internet Apr. 21, 2016. 11 pages.
Wikipedia, "Strain (biology)" https://en.wikipedia.org/wiki/Strain_(biology) Retrieved on Nov. 3, 2015. 2 pgs.
Patent Office of the Russian Federation Office Action for Russian patent application No. 2014107771/10(012274) filed on behalf of Probiotical S.P.A. dated Jun. 2, 2016. 8 pages (Russian original + English translation).

(56) References Cited

OTHER PUBLICATIONS

Restriction Requirement for U.S. Appl. No. 13/982,255, filed Nov. 12, 2013 on behalf of Giovanni Mogna. dated Oct. 17, 2014. 6 pages.
Non-Final Office Action for U.S. Appl. No. 13/982,255, filed Nov. 12, 2013 on behalf of Giovanni Mogna. dated Mar. 10, 2015. 19 pages.
Final Office Action for U.S. Appl. No. 13/982,255, filed Nov. 12, 2013 on behalf of Giovanni Mogna. dated Sep. 17, 2015. 15 pages.
Notice of Allowance for U.S. Appl. No. 13/982,255, filed Nov. 12, 2013 on behalf of Giovanni Mogna. dated Jan. 22, 2016. 10 pages.
Notice of Allowance for U.S. Appl. No. 13/982,255, filed Nov. 12, 2013 on behalf of Giovanni Mogna. dated Jun. 15, 2016. 11 pages.
Notice of Allowance for U.S. Appl. No. 13/982,255, filed Nov. 12, 2013 on behalf of Giovanni Mogna. dated Jul. 27, 2016. 9 pages.
Final Office Action for U.S. Appl. No. 14/005,821, filed Nov. 6, 2013 on behalf of Giovanni Mogna. dated Dec. 30, 2014. 30 pages.
Restriction Requirement for U.S. Appl. No. 14/117,003, filed Dec. 27, 2013 on behalf of Giovanni Mogna. dated Feb. 20, 2015. 9 pages.
Non-Final Office Action for U.S. Appl. No. 14/117,003, filed Dec. 27, 2013 on behalf of Giovanni Mogna. dated Oct. 14, 2015. 18 pages.
Final Office Action for U.S. Appl. No. 14/117,003, filed Dec. 27, 2013 on behalf of Giovanni Mogna. dated Jun. 2, 2016. 11 pages.
Restriction Requirement for U.S. Appl. No. 14/116,999, filed Dec. 20, 2013 on behalf of Giovanni Mogna. dated Mar. 11, 2015. 12 pages.
Non-Final Office Action for U.S. Appl. No. 14/116,999, filed Dec. 20, 2013 on behalf of Giovanni Mogna. dated Jun. 16, 2015. 28 pages.
Non-Final Office Action for U.S. Appl. No. 14/116,999, filed Dec. 20, 2013 on behalf of Giovanni Mogna. dated Mar. 14, 2016. 25 pages.
Restriction Requirement for U.S. Appl. No. 14/116,996, filed Dec. 18, 2013 on behalf of Giovanni Mogna. dated Feb. 4, 2015. 11 pages.
Non-Final Office Action for U.S. Appl. No. 14/116,996, filed Dec. 18, 2013 on behalf of Giovanni Mogna. dated May 21, 2015. 29 pages.
Final Office Action for U.S. Appl. No. 14/116,996, filed Dec. 18, 2013 on behalf of Giovanni Mogna. dated Mar. 7, 2016. 22 pages.
Restriction Requirement for U.S. Appl. No. 14/344,047, filed Jul. 28, 2014 on behalf of Giovanni Mogna. dated Feb. 19, 2016. 8 pages.
Restriction Requirement for U.S. Appl. No. 14/891,306, filed Nov. 13, 2015 on behalf of Giovanni Mogna. dated Apr. 13, 2016. 7 pages.
Office Action for Japanese Patent Application No. 2014-529081 dated May 31, 2016. 8 pages (Japanese original + English translation).
Cremonini, F. et al. "Effect of Different Probiotic Preparation son Anti-*Helicobacter pylori* Therapy-Related Side Effects: A Parallel Group, Triple Blind, Placebo-Controlled Study" American Journal of Gastroenterol. vol. 97; No. 11; 2002; pp. 2744-2749.
Gurbuz, A. et al. "Effect of N-Acetyl Cysteine on *Helicopacter pylori*" Southern Medical Journal; vol. 98; No. 11; Nov. 2005; pp. 1095-1097.
Candela, M. et al. "High taxonomic level fingerprint of the human intestinal microbiota by Ligase Detection Reaction—Universal Array approach" BMC Microbiology; vol. 10; No. 116; 2010; 16 pages.
Del Piano, M. et al. "Correlation Between Chronic Treatment With Proton Pump Inhibitors (PPIs) and Bacterial Overgrowth in the Stomach: Any Possible Beneficial Role for Selected Lactobacilli?" J. Clin. Gastroenterol.; vol. 48; Supp. 1; Nov./Dec. 2014; S40-S46.
Official Action for Russian Patent Application No. 2013151611 filed Apr. 18, 2012 on behalf of Giovanni Mogna. 12 pages (Russian original + English translation).

Bespalov, V.G. et al. "Biologically active food supplements" Kafedra, 2000; pp. 38-47 (Russian original + English translation of relevant parts).
Krosnyuk, I.I. et al. "Pharmaceutical technology: Technology of dosage forms: a textbook for university students" Academia editorial center; 2006; p. 6. (Russian original + English translation of relevant parts).
Khavkin, A.I. et al. "Modern principles of ulcer disease" 2009; found on the internet Mar. 29, 2016; www.lvrach.ru/2005/02/4532114/; 6 pages (Russian original + English translation of relevant parts).
"DeNol" 2009; found on the internet Mar. 29, 2016; www.rlsnet.ru/tn_index_id_6426.htm; 6 pages (Russian original + English translation of relevant parts).
T. Vasiljevic et al., "Probiotics—From Metchnikoff to bioactives", International Dairy Journal, Elsevier Applied Science, vol. 18, No. 7, Jul. 1, 2008, pp. 714-728.
J.M.T. Hamilton-Miller, "The role of probiotics in the treatment and prevention of *Helicobacter pylori* infection", International Journal of Antimicrobial Agents, vol. 22, No. 4, Oct. 2003, pp. 360-366.
Wang Kuan-Yuan, et al: "Effects of ingesting *Lactobacillus*- and *Bifidobacterium*-containing yogurt in subjects—with colonized *Helicobacter pylori*", The American Journal of Clinical Nutrition, American Society for Nutrition, US, vol. 80, No. 3, Sep. 1, 2004, pp. 737-741.
Sgouras, Dionyssios N, et al., "*Lactobacillus johnsonii* La1 attenuates *Helicobacter pylori*-associated gastritis and reduces levels of proinflammatory chemokines in C57BL/6 mice", Clinical and Diagnostic Laboratory Immunology, American Society for Microbiology, US, vol. 12, No. 12, Dec. 1, 2005, pp. 1378-1386.
PCT International Search Report dated Jul. 19, 2012 for application PCT/IB2012/000779 filed on Apr. 18, 2012 in the name of Giovanni Mogna. 5 pgs.
PCT Written Opinion dated Jul. 19, 2012 for application PCT/IB2012/000779 filed on Apr. 18, 2012 in the name of Giovanni Mogna. 5 pgs.
Germond, J.E. et al. "Evolution of the bacterial species *Lactobacillus delbrueckii:* a partial genomic study with reflections on prokaryotic concept." Mol. Biol. Evol. vol. 20(10, pp. 93-104. Jan. 2003.
Broadbent et al. "Biochemistry, Genetics, and Applications of Exopolysaccharide Production in *Streptococcus thermophiles:* A Review" J. Dairy Sci., 2003, 86, pp. 407-423.
European Patent Office Communication pursuant to Article 94(3) EPC in relation to Application No. 12 780 278.3-1401. dated Jun. 6, 2015. 4 pages.
Federici, et al. "Characterization and Heterologous Expression of the Oxalyl Coenzyme A Decarboxylase Gene from *Bifidobacterium lactis*" Applied and Environmental Microbiology, Sep. 2004; vol. 70; No. 9; pp. 5066-5073.
First Office Action for Chinese Patent Application No. 201180070870.0 dated Feb. 15, 2016. 15 pages. (Chinese original + English translation).
Guardamagna et al. "Bifidobacteria supplementation: Effects on plasma lipid profiles in dyslipidemic children" Nutrition, 2014; vol. 30; pp. 831-836.
Japanese Patent Office Official Action for Japanese Patent Application No. 2013-558517. dated Mar. 3, 2015. 4 pages. (Japanese original + English translation).
Japanese Patent Office Official Action for Japanese Patent Application No. 2014-509849. dated Apr. 26, 2016. 9 pages. (Japanese original + English translation).
Japanese Patent Office Official Action Summary for Japanese Patent Application No. 2014-509850 filed on behalf of Probiotical S.P.A. dated Feb. 16, 2016. (Japanese original + English translation) 5 pages.
Karamanolis et al. "A Glass of Water Immediately Increases Gastric pH in Healthy Subjects" Dig. Dis Sci., 2008, vol. 53, pp. 3128-3132.
Kim, H.S. et al. "In vitro Antioxidative Properties of Lactobacilli" Asian-Aust. J. Anim. Sci. 2006; vol. 19; No. 2; pp. 262-265.
Lieske, J.C. et al. "Use of a probiotic to decrease enteric hyperoxaluria" Kidney International; 2005; vol. 68; pp. 1244-1249.

(56) References Cited

OTHER PUBLICATIONS

Liu, J-R. et al. "Antioxidative Activities of Kefir" Asian-Aust. J. Anim. Sci, 2005; vol. 18. No. 4; pp. 567-573.

MacFarland, S. et al., "Review article: prebiotics in the gastrointestinal tract", Alimentary Pharmacology & Therapeutics, 2006, 24, pp. 701-714.

Masashi Okamura, "Youkei no Tomo", 2008, vol. 558, pp. 17-21 (English translation).

Mogna, L. et al. "Assessment of the in vitro inhibitory activity of specific probiotic bacteria against different *Escherichia coli* strains." Journal of Clinical Gastroenterology, vol. 46, Supp. 1, pp. S29-S32. Oct. 2012.

Office Action Inquiry for Russian Patent Application No. 2013144267 filed Mar. 17, 2011 on behalf of Probiotical S.P.A. dated Mar. 12, 2015. 5 pages. (English Translation).

Pina, D.I. et al., "Prevalence and dietetic management of mild gastrointestinal disorders in milk-fed infants", World Journal of Gastroenterology, 2008, vol. 14, No. 2: pp. 248-254.

Ronnqvist, D. et al. "*Lactobacillus fermentum* Ess-1 with unique growth inhibition of vulvo-vaginal candidiasis pathogens", Journal of Medical Microbiology (2007), 56, pp. 1500-1504.

Shigeru Kamiya, "Igaku no Ayumi" Journal of Clinical and Experimental Medicine, 2003; vol. 207; No. 10, pp. 894-898 (Japanese original + English translation).

Shu, Q. et al. "Immune protection mediated by the probiotic *Lactobacillus rhamnosus* HN001 (DR20™) against *Escherichia coli* O157:H7 infection in mice" FEMS Immunology and Medical Microbiology. 2002, 34, pp. 59-64.

Terris, M.K. et al. "Dietary Supplementation with Cranberry Concentrate Tablets May Increase the Risk of Nephrolithiasis", Urology, 2001, 57 (1), pp. 26-29.

Third Office Action for Chinese Patent Application No. 201280022854.9. dated May 17, 2016. 12 pages. (Chinese original + English translation).

Turroni, S. et al. "Oxalate consumption by lactobacilli: evaluation of oxalyl-CoA decarboxylase and formyl-CoA transferase activity in *Lactobacillus acidophilus*" Journal of Applied Microbiology; 2007; vol. 103; pp. 1600-1609.

Van Hemert, S. et al. "Influence of the Multispecies Probiotic Ecologic® Barrier on Parameters of Intestinal Barrier Function" Food and Nutrition Sciences, 2014, 5, pp. 1739-1745.

Vicariotto, F. "Effectiveness of an Association of a Cranberry Dry Extract D-mannose, and the Two Microorganisms Lactobacillus plantarum LP01 and Lactobacillus paracasei LPC09 in Women Affected by Cystitis, A Pilot Study". Journal of Clinical Gastroenterology, Nov. 2014, vol. 48, Supp.1, S96-S101.

Yoon, Y. et al. "Occurrence of Glutathione Sulphydryl (GSH) and Antioxidant Activities in Probiotic *Lactobacillus* spp." Asian-Aust. J. Anim. Sci, 2004; vol. 17; No. 11; pp. 1582-1585.

Yutaka Kanamori, "Joumyaku Keichou Eiyou (Parenteral and Enteral Nutrition)", 2010, vol. 25; No. 4, pp. 923-928 (English translation).

Anukam et al., "*Lactobacillus plantarum* and *Lactobacillus fermentum* with Probiotic Potentials Isolated from the Vagina of Healthy Nigerian Women", Research Journal of Microbiology 2(1): pp. 81-87, 2007. <academicjournals.com>.

Baluka et al., "PCR-based detection of genes responsible for oxalate detoxification in probiotic microorganisms", Annual Meeting of the Illinois State Academy of Sciences, 2008 (https://www.eiu.edu/biology/posters/2008-11.pdf). 1 page.

Corrected Notice of Allowance issued for U.S. Appl. No. 14/117,003, filed Dec. 27, 2013 on behalf of Giovanni Mogna. dated Nov. 22, 2016. 8 pages.

Final Office Action issued for U.S. Appl. No. 14/113,211, filed Nov. 26, 2013 on behalf of Giovanni Mogna. dated Nov. 22, 2016. 12 pages.

Final Office Action issued for U.S. Appl. No. 14/116,999, filed Dec. 20, 2013 on behalf of Giovanni Mogna. dated Dec. 9, 2016. 28 pages.

Final Office Action issued for U.S. Appl. No. 14/344,047, filed Jul. 28, 2014 on behalf of Giovanni Mogna. dated Aug. 4, 2017. 29 pages.

Non-Final Office Action issued for U.S. Appl. No. 14/113,211, filed Nov. 26, 2013 on behalf of Giovanni Mogna. dated Apr. 22, 2015. 13 pages.

Non-Final Office Action issued for U.S. Appl. No. 14/113,211, filed Nov. 26, 2013 on behalf of Giovanni Mogna. dated Jan. 22, 2016. 13 pages.

Non-Final Office Action issued for U.S. Appl. No. 14/344,047, filed Jul. 28, 2014 on behalf of Giovanni Mogna. dated Oct. 13, 2016. 27 pages.

Non-Final Office Action issued for U.S. Appl. No. 14/891,306, filed Nov. 13, 2015 on behalf of Probiotical S.P.A. dated Nov. 22, 2016. 37 pages.

Non-Final Office Action issued for U.S. Appl. No. 14/116,996, filed Dec. 18, 2013 on behalf of Giovanni Mogna. dated Mar. 27, 2017. 20 pages.

Non-Final Office Action issued for U.S. Appl. No. 14/346,941, filed Mar. 24, 2014 on behalf of Probiotical North America Inc. dated Apr. 19, 2017. 14 pages.

Non-Final Office Action issued for U.S. Appl. No. 15/265,706, filed Sep. 14, 2016 on behalf of Probiotical S.P.A. dated Jul. 11, 2017. 14 pages.

Non-Final Office Action issued for U.S. Appl. No. 14/891,321, filed Nov. 13, 2015 on behalf of Probiotical S.P.A. dated Sep. 6, 2017. 14 pages.

Notice of Allowance issued for U.S. Appl. No. 14/117,003, filed Dec. 27, 2013 on behalf of Giovanni Mogna. dated Nov. 9, 2016. 7 pages.

Notice of Allowance issued for U.S. Appl. No. 14/117,003, filed Dec. 27, 2013 on behalf of Giovanni Mogna. dated Jul. 6, 2017. 10 pages.

Restriction Requirement issued for U.S. Appl. No. 14/113,211, filed Nov. 26, 2013 on behalf of Giovanni Mogna. dated Sep. 5, 2014. 9 pages.

Restriction Requirement issued for U.S. Appl. No. 14/346,941, filed Mar. 24, 2014 on behalf of Probiotical North America Inc. dated Nov. 16, 2016. 8 pages.

Restriction Requirement issued for U.S. Appl. No. 14/891,321, filed Nov. 13, 2015 on behalf of Probiotical S.P.A. dated Jun. 16, 2017. 6 pages.

\* cited by examiner

COMPOSITION COMPRISING N-ACETYLCYSTEINE AND/OR MICROENCAPSULATED GASTROPROTECTED LYSOZYME IN ASSOCIATION WITH PROBIOTIC BACTERIA CAPABLE OF RESTORING THE STOMACH'S OWN BARRIER EFFECT WHICH IS LOST DURING THE PHARMACOLOGICAL TREATMENT OF GASTRIC HYPERACIDITY

BACKGROUND

In the course of the last few decades various pharmacological approaches have been developed for the pharmacological treatment of gastric hyperacidity, a condition which, if present to a marked degree and for prolonged periods, can give rise to various complications or pathologies such as peptic ulcer and gastroesophageal reflux disease.

Among the drugs most widely used are those based on active principles capable of inhibiting inhibitors of the histamine receptor $H_2$ such as, for example, cimetidine, famotidine, nizatidine, ranitidine, or based on active principles capable of inhibiting prostaglandins such as, for example, misoprostol. Another category of drugs is based on active principles which perform the function of protectors of the gastric mucosa such as, for example, bismuth salts, sucralfate or antimuscarinic or parasympatholytic drugs based on pirenzepine and pipenzolate. Finally there are also antacids such as, for example, sodium bicarbonate, aluminium hydroxide or magnesium hydroxide and proton pump inhibitors based on Lansoprazole, Esometazole, Rabeprazole, Pantoprazole and Omeprazole.

Proton pump inhibitors (PPI) are a group of molecules whose principal action consists in a pronounced reduction in the acidity of the gastric juices for a fairly long period of time (18 to 24 hours).

The group containing PPIs is the successor to $H_2$ antihistamines, and PPI inhibitors are broadly more widespread than the latter because of their greater effectiveness.

The medicines mentioned above are used in the symptomatic and aetiological treatment of various syndromes, such as: (i) dyspepsia; (ii) gastro-duodenal ulcer. PPIs are used for treating or preventing gastric and duodenal ulcers. They are also used in association with certain antibiotics in the treatment of gastritis from *Helicobacter pylori*; (iii) Zollinger-Ellison syndrome and (iv) gastroesophageal reflux disease.

PPIs are also used in patients treated long-term with acetylsalicylic acid or other NSAIDs. By inhibiting the function of the enzyme cyclooxigenase 1 (COX 1), these drugs have the side effect of reducing the synthesis of prostaglandin, a process which depends on the same enzyme. Since one of the functions of prostaglandin is the protection of the gastric mucosa from acidity, PPIs are used in order to reduce acidity and protect the gastric mucosa.

This type of medicine inhibits the gastric enzyme $H^+/K^+$-ATPase (the proton pump), catalyst of the $H^+$ and $K^-$ ion exchange. This creates effective inhibition of acid secretion.

In the micro-channel where the pH is low, close to 2, these inhibitors are ionised and transformed into molecules capable of establishing covalent bonds with the cysteine thiol group (SH) of the pump sub-unit. The pump is thus irreversibly inhibited. Renewal of pumping activity requires the production of new pumps, an event which requires 18 to 24 hours on average. A single dose of PPI, therefore, enables inhibition of the gastric secretion of about 24 hours.

The fact that the inhibitors are active only in an acid environment explains how they have a minimal effect on the extra-gastric $H^+/K^+$-ATPase situated at the level of the rectum and the colon.

In any case, apart from the specific action mechanism, the final effect of almost the totality of these classes of drugs for the treatment of gastric hyperacidity, or other pathological conditions mentioned above, is the raising of the gastric pH according to kinetics and intensities dependent on the specific molecule taken and its dosage. One exception, in this sense, is the prostaglandins and protector drugs for the gastric mucosa which, instead of reducing the intraluminal hydrogen ion concentration, increase the synthesis of mucus and bicarbonate ion by the cells of the gastric wall, thus increasing the protection of the mucosa against acidity of the lumen. In any case, drugs capable of reducing gastric hyperacidity constitute the treatment of choice in cases of peptic ulcer or gastroesophageal reflux, while mucosal protectants represent a complementary therapy.

It is known, furthermore, that normal gastric acidity constitutes an effective barrier against potential harmful organisms or pathogens ingested with the normal diet. Many of them, in fact, are particularly sensitive to acidity and are not capable of surviving for more than five minutes, sometimes even less, at pH values below 3. It follows that many pathogens, among them those belonging to the genus *Salmonella*, do not reach the intestine alive and, setting aside harmful effects on the human organism mediated by any toxins secreted and already present in food, are not capable of giving rise to an intestinal infection and, therefore, to full-blown food poisoning.

It has to be said, however, that raising the gastric pH values typically found in patients who take drugs to reduce or treat gastric hyperacidity makes these patients more exposed to dietary toxic infections caused especially by consumption of raw food, particularly fish, meat and eggs.

Patients who take drugs to reduce or treat gastric hyperacidity, such as proton pump inhibitors for example, have a stomach pH value of around 5.

This pH value allows Enterobacteriaceae, and particular strains of *E. Coli* with pronounced decarboxylasic action, to pass through the degraded gastric barrier. Proteins ingested during eating are enzymatically degraded to amino acids which, in the presence of decarboxylasic action, are modified into a series of biogenic amines ranging from potentially dangerous to highly dangerous such as for example histamine, tyramine, putrescine and cadaverine. The most common symptoms which can cause these biogenic amines have a complete overlap with the secondary effects caused by the use of proton pump inhibitors (PPIs), and are as follows: diarrhea, headache, nausea, abdominal pains and flatulence. When certain biogenic amines then react with nitrites, we have the formation of N-nitrosamines. These nitrosamines cause a genetic mutation through alkylation of the DNA, and their presence is associated with cancer of the stomach, the intestine, the pancreas and the bladder, and also with leukaemia.

One possible solution for these patients does not, obviously consist of suspension of the pharmacological treatment because this would expose the gastric or oesophageal mucosa once again to the harmful effects mediated by the gastric juices. On the other hand it is not even thinkable to continue the pharmacological treatment and leave the patients exposed to these risks of infection.

There remains, therefore, a need to allow patients in need, on the one hand, to take drugs for reducing or treating gastric hyperacidity and, on the other hand, to avoid being exposed to highly dangerous pathogenic infections or to risks of recurrent pathogenic infections.

In particular, it remains necessary to be able to respond to the above-mentioned needs by means of a composition of natural origin, free of side-effects, with an improved and selective antimicrobial efficacy against pathogens, such as for example coliforms which are a group of bacteria belonging to the family of Enterobacteriaceae and which includes, among others, *Citrobacter, Enterobacter*, preferably *Enterobacter cloacae, Escherichia*, preferably *E. coli*, including serotype O157:H7, *Hafnia, Klebsiella*, preferably *Klebsiella pneumoniae, Serratia* and *Yersinia*, or other pathogens such as the Clostridiaceae, including *Clostridium difficile, Salmonella enteriditis, Campylobacter jejuni* and *Helicobacter pylori*.

SUMMARY

The applicant has responded to the above-mentioned needs with a composition which, on the one hand, is capable of restoring the functionality of the gastric barrier, having a protective effect against pathogenic or harmful micro-organisms and, on the other, is capable of having an improved and selective efficacy against the pathogens themselves.

The present invention refers to a composition comprising N-ace cysteine and/or lysozyme or N-acetylcysteine and microencapsulated lysozyme in association with probiotic bacteria for use in the pharmacological treatment of gastric hyperacidity. Said composition is capable of restoring the stomach's own barrier effect, which is lost during the pharmacological treatment of gastric hyperacidity, and of minimising the secondary effects due to said pharmacological treatment. Furthermore, the presence of N-acetylcysteine preferably in non-microencapsulated form in said composition is capable of increasing the efficacy of the probiotic bacteria used in dealing with pathogens, and. the presence of lysozyme, preferably microencapsulated and gastroprotected, is capable of combating excessive bacterial growth and inhibiting the germination of any *clostridium* spores present without creating any kind of inhibition in relation to the probiotic bacterial flora.

DETAILED DESCRIPTION

The composition of the present invention is capable of restoring the functionality of the gastric barrier, normally exercised by the gastric juices, which is particularly reduced in patients who take drugs to reduce or treat gastric hyperacidity. Said composition is capable of minimising the secondary effects associated with pharmacological intake based on proton pump inhibitor drugs (PPIs for short). Said composition, furthermore, demonstrates improved efficacy against pathogenic or harmful micro-organisms.

After intense research activity, the Applicant has surprisingly found that a selected combination (or mixture) of probiotic bacteria comprising or, alternatively, consisting of at least one strain of bacteria belonging to one or more of the species stated below is capable of allowing patients in need, on the one hand, to take drugs for reducing or treating gastric hyperacidity and, on the other hand, to avoid being exposed to highly dangerous pathogenic infections or to risks of recurrent pathogenic infections.

The antibacterial efficacy shown by each individual strain of bacteria, the subject of the present invention, proves to be, in said composition, increased and more selective against pathogens as a result of the presence of N-acetylcysteine and/or lysozyme; or N-acetylcysteine and/or microencapsulated lysozyme. In a preferred embodiment, the lysozyme is microencapsulated in a lipid matrix. Advantageously, the lipid matrix is of vegetable origin and has a melting point comprised between 30° C. and 80° C., preferably between 40° C. and 70° C., even more preferably between 50° C. and 60° C.

The subject of the present invention consists of a composition having the characteristics stated in the attached independent claim.

Other preferred embodiments of the present invention are described in the continuation of the present description and will be claimed in the attached dependent claims.

Table 1 shows, by way of example, a group of micro-organisms which have a valid application in the context of the present invention.

Table 2 shows a group of micro-organisms which have a valid application in the context of the present invention.

Table 3 shows the results of the species-specific PCR assays carried out for identifying the bacterial species administered.

Table 4 shows the quantification of the total bacterial cells and of the total. *Lactobacillus* (value±SEM, log 10 CFU/ml of the gastric juice or gram of material from brushing the duodenum) at d0 (all groups) and at d10 (Group B).

Table 5 shows the results of the species-specific PCR assay in Group B at $d_0$ and at $d_{10}$. The presence of correlated species is shown by a "+", while their absence is shown by a "−".

Table 6 shows the quantification of the specific microbial groups in faecal samples at d0 (all groups) and d10 (Group B).

The results are expressed as log 10 of CFU/gram of faeces (value±SEM).

Figure 1:
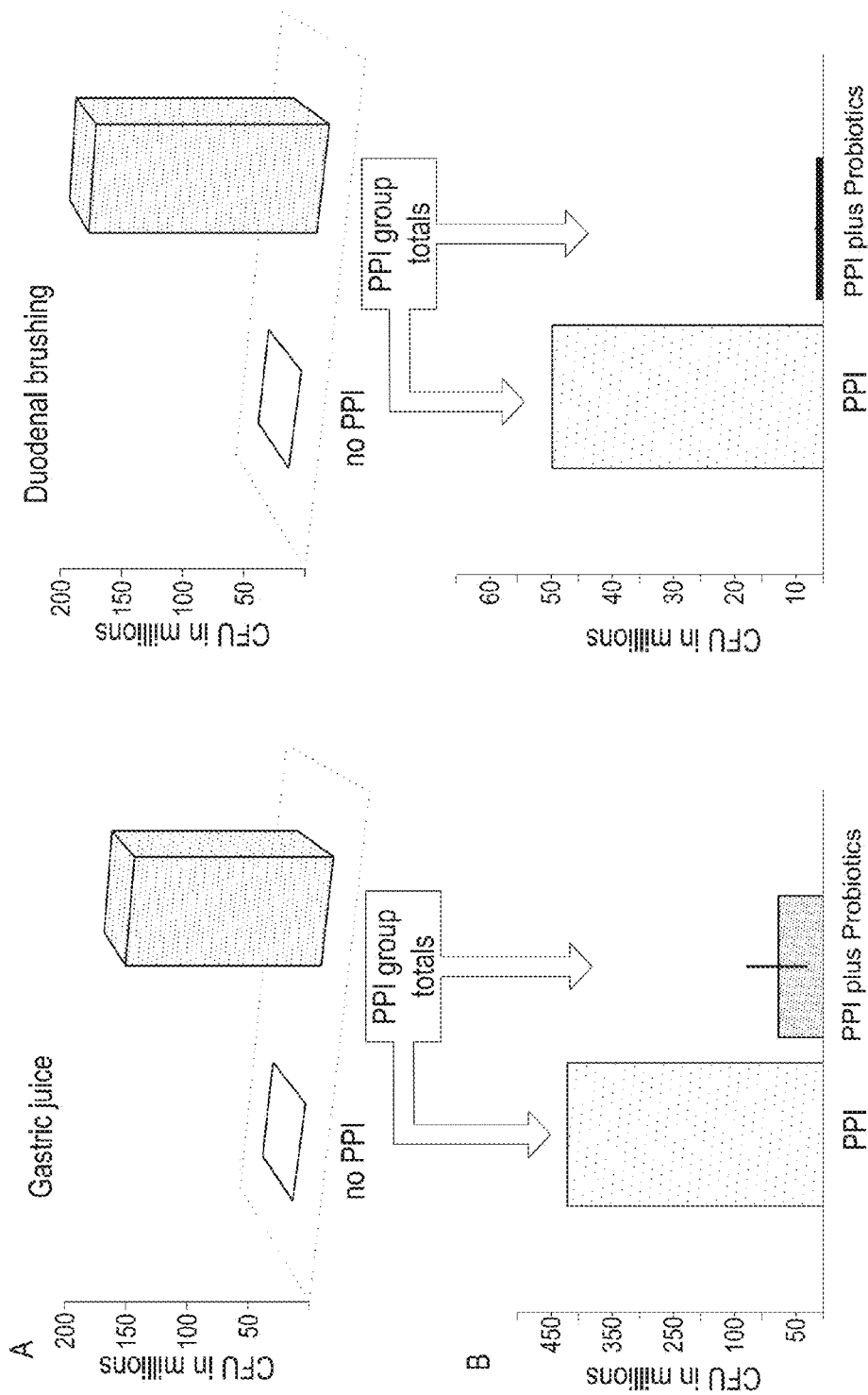
FIG. 1A shows the comparison between subjects chronically treated with PPIs (PPI group totals: PPI+"PPI plus probiotics") and the control group.
FIG. 1B shows the comparison between subjects chronically treated with PPIs and those treated with "PPIs plus probiotics") and the control group.

FIG. 1 refers to the total bacterial count present in the samples taken from the subjects of the clinical study (Figure A and Figure B).

FIG. 1A shows the comparison between subjects chronically treated with PPIs (PPI group totals: PPI+"PPI plus probiotics") and the control group. The data are expressed as an average of the colony-forming units (CFU). FIG. 1B shows the comparison between subjects chronically treated with PPIs and those treated with "PPIs plus probiotics") and the control group. The data are expressed as an average±S.E.M. of the colony-forming units (CFU).

Figure 2:
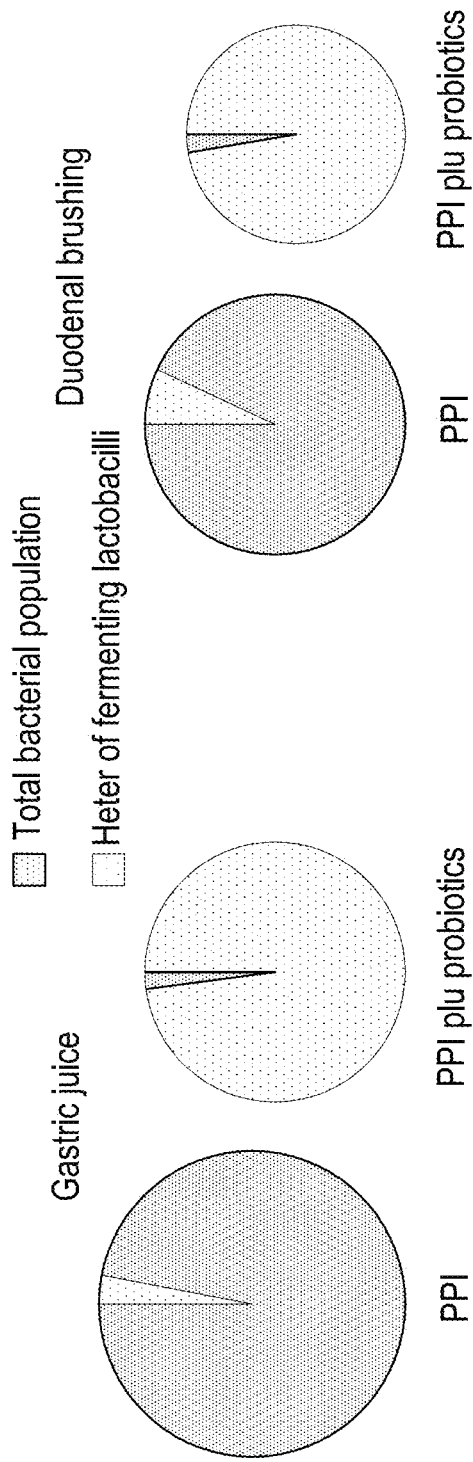
FIG. 2 shows the quantities of bacteria found in the gastric juice and after duodenal brushing in the subjects treated.

FIG. 2 shows the quantities of bacteria found in the gastric juice and after duodenal brushing in the subjects treated.

The Applicant has performed intense research and selection activity, at the end of which it found that the strains of probiotic bacteria belonging to at least one species chosen from the group comprising or, alternatively, consisting of, *L. acidophilus, L. crispatus, L. gasseri, L. delbrueckii, L. delbr.* subsp. *delbrueckii, L. salivarius, L. casei, L. paracasei, L. plantarum, L. rhamnosus, L. reuteri, L. brevis, L. buchneri, L. fermentum, L. lactis, L. pentosus, B. adolescentis, B. angulatum, B. bifidum, B. breve, B. catenulatum, B. infantis, B. lactis, B. longum, B. pseudocatenulatum* and *S. thermo-*

*philus* have a valid application in the treatment of subjects who are taking proton pump inhibitors (PPIs) to reduce or treat gastric hyperacidity. Furthermore, the Applicant has found that the antibacterial efficacy demonstrated by the strains of bacteria which are the subject of the present invention is increased and more selective against pathogens as a result of the presence of N-acetylcysteine (NAC) in said composition.

Furthermore, the Applicant has found that the antibacterial efficacy demonstrated by the strains of bacteria which are the subject of the present invention is increased and more selective against pathogens as a result of the presence of microencapsulated gastroprotected lysozyme in said composition. The lysozyme is microencapsulated in a lipid matrix. Advantageously, the lipid matrix is of vegetable origin and has a melting point comprised between 30° C. and 80° C., preferably between 40° C. and 70° C., even more preferably between 50° C. and 60° C.

Furthermore, the Applicant has found that the antibacterial efficacy demonstrated by the strains of bacteria which are the subject of the present invention is increased and more selective against pathogens as a result of the presence of N-acetylcysteine and microencapsulated gastroprotected lysozyme in said composition. The lysozyme is microencapsulated in a lipid matrix. Advantageously, the lipid matrix is of vegetable origin and has a melting point comprised between 30° C. and 80° C., preferably between 40° C. and 70° C., even more preferably between 50° C. and 60° C.

The composition of the present invention comprises N-acetylcysteine in association with the strains of bacteria of the present invention: N-acetylcysteine which is an N-acetylate derivative of the amino acid cysteine.

The composition of the present invention comprises microencapsulated gastroprotected lysozyme in association with the strains of bacteria of the present invention:

The composition of the present invention comprises N-acetylcysteine and/or microencapsulated gastroprotected lysozyme in association with the strains of bacteria of the present invention.

The Applicant has found that the use of N-acetylcysteine in association with one or two or three or four or five or six strains of bacteria, described in Tables 1 and 2, or in the various preferred embodiments here described, is capable of dissolving the bacterial biofilm produced by the pathogenic bacteria themselves and which is used by said pathogens as protection. In practice it has been seen that the pathogenic bacteria are capable of forming a protective coating (biofilm) around the cells. The biofilm makes the cells of the pathogens more difficult to attack and better protected. N-acetylcysteine is capable of penetrating the biofilm of the cells and dissolving it, facilitating the attack on the pathogenic cells by means of the bacteriocins and/or the metabolites and/or the oxygenated water produced by the strains of bacteria which are the subject of the present invention.

The Applicant has found, furthermore, that the use of microencapsulated gastroprotected lysozyme makes it possible to pass the gastro-duodenal barrier and arrive complete in the colon where it succeeds in exercising its action of inhibiting the Clostridiaceae, including *C. difficile*, thanks to the lytic action of the enzyme on the spore, in association with one or more of the strains of bacteria which are the subject of the present invention.

The quantity of N-acetylcysteine present in the composition which is the subject of the present invention is comprised between 10 and 1,000 mg/day, preferably between 50 and 200 mg/day, even more preferably between 60 and 150 mg/day. N-acetylcysteine, which is available on the market in non-microencapsulated form and in a pharmaceutically acceptable form, preferably in solid form, is mixed with the probiotic bacteria, preferably in solid or lyophilised form, using techniques and equipment known to experts in the field to give a homogeneous composition.

The quantity of microencapsulated gastroprotected lysozyme present in the composition which is the subject of the present invention is comprised between 10 and 2,000 mg/day, preferably between 400 and 1,000 mg/day, even more preferably between 500 and 800 mg/day, preferably in solid form; it is mixed with the probiotic bacteria, preferably in solid or lyophilised form, using techniques and equipment known to experts in the field, to give a homogeneous composition. Lysozyme is available on the market in a pharmaceutically acceptable form.

The strains of bacteria were selected because they are capable of colonising the stomach at a pH value comprised between 4 and 5.5; preferably between 4.5 and 5. At this pH value the selected strains act by means of the production of active substances such as bacteriocins and/or metabolites and/or oxygenated water.

The composition of the present invention can be a dietary composition, for example a symbiotic composition, or a supplement or a pharmaceutical composition or a medical device. In one embodiment, the composition can comprise or, alternatively, consist of, one or two or three or four or five or six selected strains among those listed in Table 1 or, alternatively, in Table 2, in association with N-acetylcysteine (NAC) and/or lysozyme, preferably microencapsulated lysozyme.

TABLE 1

| No. | Name | Filing no. | Date of filing | Owner |
|---|---|---|---|---|
| 1 | *Streptococcus thermophilus* B39 | LMG P-18383 | 5 May 1998 | PROBIOTICAL S.p.A |
| 2 | *Streptococus thermophilus* T003 | LMG P-18384 | 5 May 1998 | PROBIOTICAL S.p.A |
| 3 | *Lactobacillus pentosus* 9/1 ei | LMG P-21019 | 16 Oct. 2001 | MOFIN S.R.L. |
| 4 | *Lactobacillus plantarum* 776/1 bi (LP02) | LMG P-21020 | 16 Oct. 2001 | MOFIN S.R.L. |
| 5 | *Lactobacillus plantarum* 476LL 20 bi (LP01) | LMG P-21021 | 16 Oct. 2001 | MOFIN S.R.L. |
| 6 | *Lactobacillus plantarum* PR ci (LP03) | LMG P-21022 | 16 Oct. 2001 | MOFIN S.R.L. |
| 7 | *Lactobacillus plantarum* 776/2 hi (LP04) | LMG P-21023 | 16 Oct. 2001 | MOFIN S.R.L. |
| 8 | *Lactobacillus casei* ssp. *paracasei* 181A/3 aiai | LMG P-21380 | 31 Jan. 2002 | PROBIOTICAL S.p.A |

TABLE 1-continued

| No. | Name | Filing no. | Date of filing | Owner |
|---|---|---|---|---|
| 9 | *Lactobacillus* belonging to the *acidophilus* group 192A/1 aiai | LMG P-21381 | 31 Jan. 2002 | PROBIOTICAL S.p.A |
| 10 | *Bifidobacterium longum* 175A/1 aiai | LMG P-21382 | 31 Jan. 2002 | PROBIOTICAL S.p.A |
| 11 | *Bifidobacterium breve* 195A/1 aici | LMG P-21383 | 31 Jan. 2002 | PROBIOTICAL S.p.A |
| 12 | *Bifidobacterium lactis* 32A/3 aiai | LMG P-21384 | 31 Jan. 2002 | PROBIOTICAL S.p.A |
| 13 | *Lactobacillus plantarum* 501/2 gi | LMG P-21385 | 31 Jan. 2002 | MOFIN S.R.L. |
| 14 | *Lactococcus lactis* ssp. *lactis* 501/4 hi | LMG P-21387 | 15 Mar. 2002 | MOFIN S.R.L. |
| 15 | *Lactococcus lactis* ssp. *lactis* 501/4 ci | LMG P-21838 | 31 Jan. 2002 | MOFIN S.R.L. |
| 16 | *Lactobacillus plantarum* 501/4 li | LMG P-21389 | 15 Mar. 2002 | MOFIN S.R.L. |
| 17 | *Streptococcus thermophilus* GB1 | DSM 16506 | 18 Jun. 2004 | PROBIOTICAL S.p.A |
| 18 | *Streptococcus thermophilus* GB5 | DSM 16507 | 18 Jun. 2004 | PROBIOTICAL S.p.A |
| 19 | *Bifidobacterium longum* BL 03 | DSM 16603 | 20 Jul. 2004 | PROBIOTICAL S.p.A |
| 20 | *Bifidobacterium breve* BR 03 | DSM 16604 | 20 Jul. 2004 | PROBIOTICAL S.p.A |
| 21 | *Lactobacillus casei* ssp. *rhamnosus* LR 04 | DSM 16605 | 20 Jul. 2004 | PROBIOTICAL S.p.A |
| 22 | *Lactobacillus delbrueckii* ssp. *bulgaricus* LDB 01 | DSM 16606 | 20 Jul. 2004 | PROBIOTICAL S.p.A |
| 23 | *Lactobacillus delbrueckii* ssp. *bulgaricus* LDB 02 | DSM 16607 | 20 Jul. 2004 | PROBIOTICAL S.p.A |
| 24 | *Streptococcus thermophilus* Y02 | DSM 16590 | 20 Jul. 2004 | PROBIOTICAL S.p.A |
| 25 | *Streptococcus thermophilus* Y03 | DSM 16591 | 20 Jul. 2004 | PROBIOTICAL S.p.A |
| 26 | *Streptococcus thermophilus* Y04 | DSM 16592 | 20 Jul. 2004 | PROBIOTICAL S.p.A |
| 27 | *Streptococcus thermophilus* Y05 | DSM 16593 | 20 Jul. 2004 | PROBIOTICAL S.p.A |
| 28 | *Bifidobacterium adolescentis* BA 03 | DSM 16594 | 21 Jul. 2004 | PROBIOTICAL S.p.A |
| 29 | *Bifidobacterium adolescentis* BA 04 | DSM 16595 | 21 Jul. 2004 | PROBIOTICAL S.p.A |
| 30 | *Bifidobacterium breve* BR 04 | DSM 16596 | 21 Jul. 2004 | PROBIOTICAL S.p.A |
| 31 | *Bifidobacterium Pseudocatenulatum* BP 01 | DSM 16597 | 21 Jul. 2004 | PROBIOTICAL S.p.A |
| 32 | *Bifidobacterium Pseudocatenulatum* BP 02 | DSM 16598 | 21 Jul. 2004 | PROBIOTICAL S.p.A |
| 33 | *Staphylococcus xylosus* SX 01 | DSM 17102 | 1 Feb. 2005 | PROBIOTICAL S.p.A |
| 34 | *Bifidobacterium adolescentis* BA 02 | DSM 17103 | 1 Feb. 2005 | PROBIOTICAL S.p.A |
| 35 | *Lactobacillus plantarum* LP 07 | DSM 17104 | 1 Feb. 2005 | PROBIOTICAL S.p.A |
| 36 | *Streptococcus thermophilus* YO8 | DSM 17843 | 21 Dec. 2005 | PROBIOTICAL S.p.A |
| 37 | *Streptococcus thermophilus* YO9 | DSM 17844 | 21 Dec. 2005 | PROBIOTICAL S.p.A |
| 38 | *Streptococcus thermophilus* YO100 | DSM 17845 | 21 Dec. 2005 | PROBIOTICAL S.p.A |
| 39 | *Lactobacillus fermentum* LF06 | DSM 18295 | 24 May 2006 | PROBIOTICAL S.p.A |
| 40 | *Lactobacillus fermentum* LF07 | DSM 18296 | 24 May 2006 | PROBIOTICAL S.p.A |
| 41 | *Lactobacillus fermentum* LF08 | DSM 18297 | 24 May 2006 | PROBIOTICAL S.p.A |
| 42 | *Lactobacillus fermentum* LF09 | DSM 18298 | 24 May 2006 | PROBIOTICAL S.p.A |
| 43 | *Lactobacillus gasseri* LGS01 | DSM 18299 | 24 May 2006 | PROBIOTICAL S.p.A |
| 44 | *Lactobacillus gasseri* LGS02 | DSM 18300 | 24 May 2006 | PROBIOTICAL S.p.A |
| 45 | *Lactobacillus gasseri* LGS03 | DSM 18301 | 24 May 2006 | PROBIOTICAL S.p.A |
| 46 | *Lactobacillus gasseri* LGS04 | DSM 18302 | 24 May 2006 | PROBIOTICAL S.p.A |

TABLE 1-continued

| No. | Name | Filing no. | Date of filing | Owner |
|---|---|---|---|---|
| 47 | *Bifidobacterium adolescentis* (reclassified 11.05.2009 as *Bifidobacterium catenulatum* sp./*pseudocatenulatum* 31, ID 09-255) | DSM 18350 | 15 Jun. 2006 | PROBIOTICAL S.p.A |
| 48 | *Bifidobacterium adolescentis* EI-15 | DSM 18351 | 15 Jun. 2006 | PROBIOTICAL S.p.A |
| 49 | *Bifidobacterium adolescentis* EI-18 (reclassfied 11.05.2009 as *Bifidobacterium animalis* subsp. *lactis* EI-18, ID 09-256) | DSM 18352 | 15 Jun. 2006 | PROBIOTICAL S.p.A |
| 50 | *Bifidobacterium catenulatum* EI-20 | DSM 18353 | 15 Jun. 2006 | PROBIOTICAL S.p.A |
| 51 | *Streptococcus thermophilus* FRai | DSM 18613 | 13 Sep. 2006 | MOFIN S.R.L. |
| 52 | *Streptococcus thermophilus* LB2bi | DSM 18614 | 13 Sep. 2006 | MOFIN S.R.L. |
| 53 | *Streptococcus thermophilus* LRci | DSM 18615 | 13 Sep. 2006 | MOFIN S.R.L. |
| 54 | *Streptococcus thermophilus* FP4 | DSM 18616 | 13 Sep. 2006 | MOFIN S.R.L. |
| 55 | *Streptococcus thermophilus* ZZ5F8 | DSM 18617 | 13 Sep. 2006 | MOFIN S.R.L. |
| 56 | *Streptococcus thermophilus* TEO4 | DSM 18618 | 13 Sep. 2006 | MOFIN S.R.L. |
| 57 | *Streptococcus thermophilus* S1ci | DSM 18619 | 13 Sep. 2006 | MOFIN S.R.L. |
| 58 | *Streptococcus thermophilus* 641bi | DSM 18620 | 13 Sep. 2006 | MOFIN S.R.L. |
| 59 | *Streptococcus thermophilus* 277A/1ai | DSM 18621 | 13 Sep. 2006 | MOFIN S.R.L. |
| 60 | *Streptococcus thermophilus* 277A/2ai | DSM 18622 | 13 Sep. 2006 | MOFIN S.R.L. |
| 61 | *Streptococcus thermophilus* IDC11 | DSM 18623 | 13 Sep. 2006 | MOFIN S.R.L. |
| 62 | *Streptococcus thermophilus* ML3di | DSM 18624 | 13 Sep. 2006 | MOFIN S.R.L. |
| 63 | *Streptococcus thermophilus* TEO3 | DSM 18625 | 13 Sep. 2006 | MOFIN S.R.L. |
| 64 | *Streptococcus thermophilus* G62 | DSM 19057 | 21 Feb. 2007 | MOFIN S.R.L. |
| 65 | *Streptococcus thermophilus* G1192 | DSM 19058 | 21 Feb. 2007 | MOFIN S.R.L. |
| 66 | *Streptococcus thermophilus* GB18 | DSM 19059 | 21 Feb. 2007 | MOFIN S.R.L. |
| 67 | *Streptococcus thermophilus* CCR21 | DSM 19060 | 21 Feb. 2007 | MOFIN S.R.L. |
| 68 | *Streptococcus thermophilus* G92 | DSM 19061 | 21 Feb. 2007 | MOFIN S.R.L. |
| 69 | *Streptococcus thermophilus* G69 | DSM 19062 | 21 Feb. 2007 | MOFIN S.R.L. |
| 70 | *Streptococcus thermophilus* YO 10 | DSM 19063 | 21 Feb. 2007 | PROBIOTICAL S.p.A |
| 71 | *Streptococcus thermophilus* YO 11 | DSM 19064 | 21 Feb. 2007 | PROBIOTICAL S.p.A |
| 72 | *Streptococcus thermophilus* YO 12 | DSM 19065 | 21 Feb. 2007 | PROBIOTICAL S.p.A |
| 73 | *Streptococcus thermophilus* YO 13 | DSM 19066 | 21 Feb. 2007 | PROBIOTICAL S.p.A |
| 74 | *Weissella* ssp. WSP 01 | DSM 19067 | 21 Feb. 2007 | PROBIOTICAL S.p.A |
| 75 | *Weissella* ssp. WSP 02 | DSM 19068 | 21 Feb. 2007 | PROBIOTICAL S.p.A |
| 76 | *Weissella* ssp. WSP 03 | DSM 19069 | 21 Feb. 2007 | PROBIOTICAL S.p.A |
| 77 | *Lactobacillus plantarum* LP 09 | DSM 19070 | 21 Feb. 2007 | PROBIOTICAL S.p.A |
| 78 | *Lactococcus lactis* NS 01 | DSM 19072 | 21 Feb. 2007 | PROBIOTICAL S.p.A |
| 79 | *Lactobacillus plantarum* LP 10 | DSM 19071 | 21 Feb. 2007 | PROBIOTICAL S.p.A |
| 80 | *Lactobacillus fermentum* LF 10 | DSM 19187 | 20 Mar. 2007 | PROBIOTICAL S.p.A |
| 81 | *Lactobacillus fermentum* LF 11 | DSM 19188 | 20 Mar. 2007 | PROBIOTICAL S.p.A |
| 82 | *Lactobacillus casei* ssp. *rhamnosus* LR 05 | DSM 19739 | 27 Sep. 2007 | PROBIOTICAL S.p.A |

TABLE 1-continued

| No. | Name | Filing no. | Date of filing | Owner |
|---|---|---|---|---|
| 83 | *Bifidobacterium bifidum* BB01 | DSM 19818 | 30 Oct. 2007 | PROBIOTICAL S.p.A |
| 84 | *Lactobacillus delbrueckii* LD 01 | DSM 19948 | 28 Nov. 2007 | PROBIOTICAL S.p.A |
| 85 | *Lactobacillus delbrueckii* LD 02 | DSM 19949 | 28 Nov. 2007 | PROBIOTICAL S.p.A |
| 86 | *Lactobacillus delbrueckii* LD 03 | DSM 19950 | 28 Nov. 2007 | PROBIOTICAL S.p.A |
| 87 | *Lactobacillus delbrueckii* LD 04 | DSM 19951 | 28 Nov. 2007 | PROBIOTICAL S.p.A |
| 88 | *Lactobacillus delbrueckii* LD 05 | DSM 19952 | 28 Nov. 2007 | PROBIOTICAL S.p.A |
| 89 | *Bifidobacterium pseudocatenulatum* B660 | DSM 21444 | 13 May 2008 | PROBIOTICAL S.p.A |
| 90 | *Lactobacillus acidophilus* LA 02 | DSM 21717 | 6 Aug. 2008 | PROBIOTICAL S.p.A |
| 91 | *Lactobacillus paracasei* LPC 08 | DSM 21718 | 6 Aug. 2008 | PROBIOTICAL S.p.A |
| 92 | *Lactobacillus pentosus* LPS 01 | DSM 21980 | 14 Nov. 2008 | PROBIOTICAL S.p.A |
| 93 | *Lactobacillus rhamnosus* LR 06 | DSM 21981 | 14 Nov. 2008 | PROBIOTICAL S.p.A |
| 94 | *Lactobacillus delbrueckii* ssp. *delbrueckii* DSMZ 20074 | DSM 22106 | | PROBIOTICAL S.p.A |
| 95 | *Lactobacillus plantarum* LP1 | DSM 22107 | 10 Dec. 2008 | PROBIOTICAL S.p.A |
| 96 | *Lactobacillus salivarius* LS01 | DSM 22775 | 23 Jul. 2009 | PROBIOTICAL S.p.A |
| 97 | *Lactobacillus salivarius* LS06 | DSM 22776 | 23 Jul. 2009 | PROBIOTICAL S.p.A |
| 98 | *Bifidobacterium bifidum* BB01 | DSM 22892 | 28 Aug. 2009 | PROBIOTICAL S.p.A |
| 99 | *Bifidobacterium bifidum* | DSM 22893 | 28 Aug. 2009 | PROBIOTICAL S.p.A |
| 100 | *Bifidobacterium bifidum* BB03 | DSM 22894 | 28 Aug. 2009 | PROBIOTICAL S.p.A |
| 101 | *Bifidobacterium lactis* BS05 | DSM 23032 | 13 Oct. 2009 | PROBIOTICAL S.p.A |
| 102 | *Lactobacillus acidophilus* LA06 | DSM 23033 | 13 Oct. 2009 | PROBIOTICAL S.p.A |
| 103 | *Lactobacillus brevis* LBR01 | DSM 23034 | 13 Oct. 2009 | PROBIOTICAL S.p.A |
| 104 | *Bifidobacterium animalis/lactis* BS06 | DSM 23224 | 12 Jan. 2010 | PROBIOTICAL S.p.A |
| 105 | *Bifidobacterium longum* BL05 | DSM 23234 | 12 Jan. 2010 | PROBIOTICAL S.p.A |
| 106 | *Bifidobacterium longum* BL04 | DSM 23233 | 12 Jan. 2010 | PROBIOTICAL S.p.A |
| 107 | *Bifidobacterium bifidum* MB109 | DSM 23731 | 29 Jun. 2010 | PROBIOTICAL S.p.A |
| 108 | *Bifidobacterium breve* MB113 | DSM 23732 | 29 Jun. 2010 | PROBIOTICAL S.p.A |
| 109 | *Bifidobacterium lactis* B2409 | DSM 23733 | 29 Jun. 2010 | PROBIOTICAL S.p.A |
| 110 | *Lactobacillus reuteri* LRE01 | DSM 23877 | 5 Aug. 2010 | PROBIOTICAL S.p.A |
| 111 | *Lactobacillus reuteri* LRE02 | DSM 23878 | 5 Aug. 2010 | PROBIOTICAL S.p.A |
| 112 | *Lactobacillus reuteri* LRE03 | DSM 23879 | 5 Aug. 2010 | PROBIOTICAL S.p.A |
| 113 | *Lactobacillus reuteri* LRE04 | DSM 23880 | 5 Aug. 2010 | PROBIOTICAL S.p.A |
| 114 | *Lactobacillus paracasei* ssp. *paracasei* LPC09 | DSM 24243 | 23 Nov. 2010 | PROBIOTICAL S.p.A |
| 115 | *Lactobacillus acidophilus* LA07 | DSM 24303 | 23 Nov. 2010 | PROBIOTICAL S.p.A |
| 116 | *Bifidobacterium bifidum* BB04 | DSM 24437 | 4 Jan. 2011 | PROBIOTICAL S.p.A |
| 117 | *Lactobacillus salivarius* LS04 | DSM 24618 | 2 Mar. 2011 | PROBIOTICAL S.p.A |
| 118 | *Lactobacillus crispatus* LCR01 | DSM 24619 | 2 Mar. 2011 | PROBIOTICAL S.p.A |
| 119 | *Lactobacillus crispatus* LCR02 | DSM 24620 | 2 Mar. 2011 | PROBIOTICAL S.p.A |
| 120 | *Lactobacillus acidophilus* LA09 | DSM 24621 | 2 Mar. 2011 | PROBIOTICAL S.p.A |
| 121 | *Lactobacillus gasseri* LGS05 | DSM 24622 | 2 Mar. 2011 | PROBIOTICAL S.p.A |

TABLE 1-continued

| No. | Name | Filing no. | Date of filing | Owner |
|---|---|---|---|---|
| 122 | Lactobacillus paracasei LPC11 | DSM 24623 | 2 Mar. 2011 | PROBIOTICAL S.p.A |
| 123 | Bifidobacterium infantis B102 | DSM 24687 | 29 Mar. 2011 | PROBIOTICAL S.p.A |
| 124 | Bifidobacterium bifidum BB06 | DSM 24688 | 29 Mar. 2011 | PROBIOTICAL S.p.A |
| 125 | Bifidobacterium longum BL06 | DSM 24689 | 29 Mar. 2011 | PROBIOTICAL S.p.A |
| 126 | Bifidobacterium lactis BS07 | DSM 24690 | 29 Mar. 2011 | PROBIOTICAL S.p.A |
| 127 | Bifidobacterium longum PCB133 | DSM 24691 | 29 Mar. 2011 | PROBIOTICAL S.p.A |
| 128 | Bifidobacterium breve B632 | DSM 24706 | 7 Apr. 2011 | PROBIOTICAL S.p.A |
| 129 | Bifidobacterium breve B2274 | DSM 24707 | 7 Apr. 2011 | PROBIOTICAL S.p.A |
| 130 | Bifidobacterium breve B7840 | DSM 24708 | 7 Apr. 2011 | PROBIOTICAL S.p.A |
| 131 | Bifidobacterium longum B1975 | DSM 24709 | 7 Apr. 2011 | PROBIOTICAL S.p.A |
| 132 | Lactobacillus reuteri | DSM 17938 | | BIOGAIA |
| 133 | Lactobacillus reuteri | ATCC 55730 | | BIOGAIA |
| 134 | Lactobacillus reuteri | PTA ATCC 6475 | | BIOGAIA |
| 135 | Lactobacillus rhamnosus GG | ATCC 53103 | | GORBACH/GOLDIN |
| 136 | Bifidobacterium animalis ssp. lactis BB-12 ® | DSM 15954 | | CHR. HANSEN |
| 137 | Lactobacillus casei Shirota | FERM BP-1366 | | YAKULT |
| 138 | Lactobacillus plantarum 299v | DSM 9843 | | INSTITUT ROSELL |
| 139 | Lactobacillus paracasei ssp. paracasei CRL-431 | ATCC 55544 | | CERELA |
| 140 | Lactobacillus crispatus P 17631 | LMG P-17631 | | PROGE FARM S.r.L. |
| 141 | Lactobacillus acidophilus P 18806 | LMG P-18806 | | PROGE FARM S.r.L. |
| 142 | Lactobacillus delbrueckii P 18805 | LMG P-18805 | | PROGE FARM S.r.L. |
| 143 | Lactobacillus gasseri P 17632 | LMG P-17632 | | PROGE FARM S.r.L. |
| 144 | Lactobacillus gasseri P 18137 | LMG P-18137 | | PROGE FARM S.r.L. |
| 145 | Lactobacillus paracasei I1688 | CNCM I-1688 | | PROGE FARM S.r.L. |
| 146 | Lactobacillus plantarum P 17630 | LMG P-17630 | | PROGE FARM S.r.L. |
| 147 | Lactobacillus salivarius I1794 | CNCM I-1794 | | PROGE FARM S.r.L. |
| 148 | Bifidobacterium longum BB536 | BAA-999TM | | MORINAGA MILK INDUSTRY CO., LTD |

The composition comprises from one to six strains, preferably from two to five strains, even more preferably four strains among those listed in Table 1 and in Table 2. Strains particularly preferred are chosen from among those listed in Table 2.

TABLE 2

| Strain | Filing no. | Pathogen antagonised | Owner of strain |
|---|---|---|---|
| Lactobacillus pentosus LPS 01 | DSM 21980 | Escherichia coli, coliforms | Probiotical S.p.A. |
| Lactobacillus plantarum LP 01 | LMG P-21021 | Escherichia coli, Listeria monocytogenes | Probiotical S.p.A. |
| Lactobacillus plantarum LP 02 | LMG P-21020 | Escherichia coli, Listeria monocytogenes | Probiotical S.p.A. |
| Lactobacillus plantarum LP 03 | LMG P-21022 | Escherichia coli, Listeria monocytogenes | Probiotical S.p.A. |
| Lactobacillus plantarum LP 04 | LMG P-21023 | Escherichia coli, Listeria monocytogenes | Probiotical S.p.A. |

TABLE 2-continued

| Strain | Filing no. | Pathogen antagonised | Owner of strain |
|---|---|---|---|
| Lactobacillus pentosus LPS 01 | DSM 21980 | Producer of bacteriocins and oxygenated water | Probiotical S.p.A. |
| Lactobacillus fermentum LF 5 | CNCM I-789 | Candida albicans, Candida krusei, Candida glabrata, Candida parapsilosis | Probiotical S.p.A. |
| Lactobacillus fermentum LF 10 | DSM 19187 | Candida albicans, Candida krusei, Candida glabrata, Candida parapsilosis, Salmonella, Staphylococcus aureus | Probiotical S.p.A. |
| Lactobacillus fermentum LF 09 | DSM 18298 | Candida albicans | Probiotical S.p.A. |
| Lactobacillus fermentum LF 11 | DSM 19188 | Candida albicans, Candida krusei, Candida glabrata, Candida parapsilosis | Probiotical S.p.A. |
| Lactococcus lactis NS 01 | DSM 19072 | Bacillus brevis, Bacillus cereus, Bacillus coagulans, Enterococcus faecalis and faecium, Staphylococcus aureus, Clostridium botulinum, Clostridium butyricum, Listeria | Probiotical S.p.A. |
| Lactobacillus salivarius LS04 | DSM 24618 | Candida, Enterococcus faecalis and faecium, Neisseria gonorrhoeae | Probiotical S.p.A. |
| Lactobacillus crispatus LCR01 | DSM 24619 | Powerful producer of oxygenated water/non-specific and broad-spectrum inhibition | Probiotical S.p.A. |
| Lactobacillus crispatus LCR02 | DSM 24620 | Powerful producer of oxygenated water/non-specific and broad-spectrum inhibition | Probiotical S.p.A. |
| Lactobacillus acidophilus LA09 | DSM 24621 | Candida, by coaggregation | Probiotical S.p.A. |
| Lactobacillus gasseri LGS05 | DSM 24622 | Powerful producer of lactic acid/non-specific and broad-spectrum inhibition | Probiotical S.p.A. |
| Lactobacillus paracasei LPC11 | DSM 24623 | Staphylococcus aureus Powerful producer of oxygenated water/non-specific and broad-spectrum inhibition | Probiotic |
| Lactobacillus rhamnosus LR06 | DSM 21981 | Candida krusei, Candida albicans, Candida glabrata, Escherichia coli, Gardnerella vaginalis | Probiotical S.p.A. |
| Lactobacillus reuteri | DSM 17938 | Escherichia coli, other coliforms, Helicobacter pylori, Listeria monocytogenes, | BioGaia |
| Lactobacillus reuteri | PTA ATCC 6475 | | BioGaia |
| Lactobacillus reuteri LRE 01 | DSM 23877 | Salmonella typhimurium, Pseudomonas aeruginosa, Shigella spp, Campylobacter jejuni, Bacillus subtilis, Clostridium perfringens, Candida albicans, Aspergillus flavus, Tripanosoma cruzi, Eimeria tenella | Probiotical S.p.A. |
| Lactobacillus reuteri LRE 02 | DSM 23878 | | Probiotical S.p.A. |
| Lactobacillus reuteri LRE 03 | DSM 23879 | | Probiotical S.p.A. |
| Lactobacillus reuteri LRE 04 | DSM 23880 | | Probiotical S.p.A. |
| Lactobacillus reuteri | ATCC 5730 | | BIOGAIA |
| Lactobacillus delbrueckii ssp. delbrueckii DSMZ 20074 | DSM 22106 | Klebsiella oxytoca, Enterobacter cloacae, Klebsiella pneumoniae, Escherichia coli | Probiotical S.p.A. |
| Bifidobacterium longum PCB 133 | DSM 24691 | Campylobacter jejuni | Probiotical S.p.A. |
| Bifidobacterium longum BL06 | DSM 24689 | Campylobacter jejuni | Probiotical S.p.A. |
| Bifidobacterium longum B1975 | DSM 24709 | Klebsiella oxytoca, Enterobacter cloacae, | Probiotical S.p.A. |
| Bifidobacterium breve B2274 | DSM 24707 | Klebsiella pneumoniae, Escherichia coli | Probiotical S.p.A. |
| Bifidobacterium breve B632 | DSM 24706 | | Probiotical S.p.A. |
| Bifidobacterium breve B7840 | DSM 24708 | | Probiotical S.p.A. |

The strains of Table 2 have been individually tested for the purpose of identifying the pathogen which they are capable of antagonising (inhibiting the growth or reducing the number of one or more harmful or pathogenic microbial species/genus), as stated in column 3 of Table 2.

Table 2 shows that the bacteria are capable of producing oxygenated water or at least one bacteriocin with an inhibiting action on one or more harmful or pathogenic microbial species/genus.

All the strains described and/or claimed in the present patent application have been deposited in accordance with the Treaty of Budapest and are made available to the public on request to the competent Depositing Authority.

The compositions of the present invention have a valid application for use both in the treatment of subjects who are taking drugs to reduce and/or treat gastric hyperacidity and in the treatment of an ulcer caused by a deficiency in the protective mechanisms of the mucosa (e.g. reduced secretion or responsiveness to prostaglandin E, as in the case of taking aspirin or other NSAIs) or by an infection by *H. pylori*. In other words, the composition of the present invention has a valid application also for those subjects who are prescribed PPIs/other antacid drugs although not showing gastric hyperacidity, but with a lesion of the gastric and/or duodenal mucosa consequent on an altered ratio of gastric acidity/mechanisms protecting the mucosa.

It has been found that the compositions of the present invention are capable of being validly used in the treatment of peptic ulcer or gastroesophageal reflux.

In one embodiment, the composition comprises or, alternatively, consists of from one to six strains, preferably from two to five strains, even more preferably from three to four strains, chosen from among the strains of probiotic bacteria belonging to at least one species chosen from the group comprising or, alternatively, consisting of, *L. acidophilus, L. crispatus, L. gasseri, L. delbrueckii, L. delbr.* subsp. *delbrueckii, L. salivarius, L. casei, L. paracasei, L. plantarum, L. rhamnosus, L. reuteri, L. brevis, L. buchneri, L. fermentum, L. lactis, L. pentosus, B. adolescentis, B. angulatum, B. bifidum, B. breve, B. catenulatum, B. infantis, B. lactis, B. longum, B. pseudocatenulatum* and *S. thermophilus* in association with N-acetylcysteine and/or lysozyme; or N-acetylcysteine and microencapsulated lysozyme.

In one embodiment, the composition comprises or, alternatively, consists of from one to six strains, preferably from two to five strains, even more preferably from three to four strains, chosen from among the strains of probiotic bacteria belonging to one or more species chosen from the group comprising or, alternatively, consisting of *L. delbrueckii, L. delbr.* subsp. *delbrueckii, L. plantarum, L. rhamnosus, L. pentosus, B. breve* and *B. longum* in association with N-acetylcysteine and/or lysozyme; or N-acetylcysteine and microencapsulated lysozyme.

In one embodiment, the composition comprises or, alternatively, consists of from one to six strains, preferably from two to five strains, even more preferably from three to four strains, chosen from the group comprising or, alternatively, consisting of:

1. *Lactobacillus pentosus* LPS01 DSM 21980
2. *Lactobacillus plantarum* LP01 LMG P-21021
3. *Lactobacillus plantarum* LP02 LMG P-21020
4. *Lactobacillus plantarum* LP03 LMG P-21022
5. *Lactobacillus plantarum* LP04 LMG P-21023
6. *Lactobacillus rhamnosus* LR06 DSM 21981
7. *Lactobacillus delbrueckii* LDD 01 (DSMZ 20074) DSM 22106
8. *Bifidobacterium longum* B1975 DSM 24709
9. *Bifidobacterium breve* 82274 DSM 24707
10. *Bifidobacterium breve* B632 DSM 24706
11. *Bifidobacterium breve* B7840 DSM 24708
12. *Bifidobacterium longum* PCB 133 DSM 24691
13. *Bifidobacterium longum* BL06 DSM 24689 in association with N-acetylcysteine and/or lysozyme; or N-acetylcysteine and microencapsulated lysozyme.

In one embodiment, the composition comprises or, alternatively, consists of from one to six strains, preferably from two to five strains, even more preferably from three to four strains, chosen from among the strains of probiotic bacteria belonging to one or more species chosen from the group comprising or, alternatively, consisting of *L. delbrueckii, L. delbr* subsp. *delbrueckii, L. plantarum, L. rhamnosus* and *L. pentosus* in association with N-acetylcysteine and/or lysozyme; or N-acetylcysteine and/or lysozyme; or N-acetylcysteine and microencapsulated lysozyme.

In one embodiment, the composition comprises or, alternatively, consists of from one to four strains, chosen from the group comprising or, alternatively, consisting of:

*Lactobacillus pentosus* LPS01 DSM 21980
*Lactobacillus plantarum* LP01 LMG P-21021
*Lactobacillus rhamnosus* LR06 DSM 21981
*Lactobacillus delbrueckii* subsp. *delbrueckii* LDD01 (MB386) DSMZ 20074 DSM 22106 in association with N-acetylcysteine and/or lysozyme; or N-acetylcysteine and microencapsulated lysozyme.

In the context of the present invention, the compositions may comprise a single strain belonging to each individual species listed above or, alternatively, may comprise more than one strain belonging to the same species, as for example two strains, or three strains, or four strains, all belonging to the same species, as shown above.

In one embodiment, the composition comprises *Lactobacillus pentosus* LPS01 DSM 21980 and/or *Lactobacillus plantarum* LP01 LMG P-21021 and/or *Lactobacillus rhamnosus* LR06 DSM 21981 and/or *Lactobacillus delbrueckii* subsp. *delbrueckii* (MB386) LDD01 DSMZ 20074 (DSM 22106) in a quantity comprised between $1\times10^9$ and $10\times10^9$ CFU/strain/dose, preferably between 3 and $5\times10^9$ CFU/strain/dose; NAC in a quantity comprised between 10 and 200 mg, preferably between 50 and 150 mg/dose, even more preferably between 60 and 100 mg/dose; potato maltodextrin in a quantity comprised between 1 and 5 grams/dose, preferably between 2 and 3 grams/dose.

The compositions described above are for use in the preventive and/or curative treatment of infections, disturbances or illnesses caused by the presence of *Helicobacter pylori*, in particular in the preventive and/or curative treatment of recurrences from infections caused by *Helicobacter pylori*; they are furthermore for use in the treatment of peptic ulcer or gastroesophageal reflux.

In another embodiment, the composition of the present invention comprises or, alternatively, consists of from one to six strains, preferably from two to five strains, even more preferably from three to four, chosen from among those above indicated by the numbers 1 to 13, in association with the strain *Lactobacillus fermentum* LF 09 DSM 18298 and/or the strain *Lactococcus lactis* NS 01 DSM 19072.

In another embodiment, the composition of the present invention comprises or, alternatively, consists of from one to six strains, preferably from two to five strains, even more preferably from three to four, chosen from among those above indicated by the numbers 1 to 13, in association with at least one strain chosen from the group comprising or, alternatively, consisting of: (a) *Lactobacillus reuteri* LRE 01

DSM 23877; (b) *Lactobacillus reuteri* LRE 02 DSM 23878; (c) *Lactobacillus reuteri* LRE 03 DSM 23879; (d) *Lactobacillus reuteri* LRE 04 DSM 23880.

The selected strains of the present invention are capable of producing bacteriocins and/or metabolites and/or oxygenated water, these being substances which are capable of effectively combating, inhibiting or reducing pathogenic bacteria. These strains find valid application and use in the preventive and/or curative treatment of infections and/or pathologies connected with pathogenic gram-negative bacteria.

The pathogenic bacteria are chosen from the group comprising the coliforms. The coliforms are a group of bacteria belonging to the family of Enterobacteriaceae. The group comprises more than fifty genera, among them *Citrobacter, Enterobacter*, preferably *Enterobacter cloacae, Escherichia*, preferably *E. coli*, including the serotype O157:H7, *Hafnia, Klebsiella*, preferably *Klebsiella pneumoniae, Serratia* and *Yersinia*. Other pathogens always of interest in the context of the present invention belong to the species chosen from the group comprising Clostridiaceae, *C. difficile* included, *Salmonella enteriditis, Campylobacter jejuni* and *Helicobacter pylori*. In a preferred embodiment, the pharmaceutical or dietary composition or the supplement or the medical device may comprise at least one strain of bacteria belonging to one or more species chosen from the group comprising or, alternatively, consisting of: *Lactobacillus delbrueckii, Lactobacillus delbrueckii* subsp. *delbrueckii, Lactobacillus plantarum, Lactobacillus rhamnosus, Lactobacillus pentosus, Lactobacillus reuteri* and *Bifidobacterium breve* in association with N-acetylcysteine and/or lysozyme; or N-acetylcysteine and microencapsulated lysozyme. Said strain is capable of producing bacteriocins and/or metabolites and/or oxygenated water. Said composition has a valid application in the preventive and/or curative treatment of infections and/or pathologies connected with *E. coli* pathogens. The pathogen *E. coli* is chosen from among *E. coli* O157:H7 and *E. coli* O104:H4. Preferably, the pathogen *E. coli* is chosen from the group comprising *E. coli* ATCC 8739, *E. coli* ATCC 10536, *E. coli* ATCC 35218 and *E. coli* ATCC 25922. A further pathogen antagonised by the strains of bacteria of the present invention is *Clostridium difficile*. In a preferred embodiment, said at least one strain of bacteria is chosen from the group comprising or, alternatively, consisting of *B. breve* BR03 DSM 16604, *B. breve* B632 DSM 24706, *L. rhamnosus* LR04 DSM 16605, *L. rhamnosus* LR06 DSM 21981, *L. plantarum* LP01 LMG P-21021, *L. plantarum* LP02 LMG P-21020, *L. pentosus* LPS01 DSM 21980, *L. delbr.* subsp. *delbrueckii* LDD01 DSMZ 20074 DSM 22106. Even more preferably, said at least one strain is chosen from the group comprising or, alternatively, consisting of *L. rhamnosus* LR06 DSM 21981, *L. plantarum* LP01 LMG P-21021, *L. pentosus* LPS01 DSM 21980 and *L. delbr.* subsp. *delbrueckii* LDD01 DSM 22106; these strains have been tested in vitro against the serotype 0157:H7 and have demonstrated strong antagonistic activity. It has been found that a composition comprising *Lactobacillus pentosus* LPS01 DSM 21980, *Lactobacillus plantarum* LP01 LMG P-21021, *Lactobacillus rhamnosus* LR06 DSM 21981 and *Lactobacillus delbrueckii* LDD 01 (MB386) DSM 20074 *Lactobacillus delbrueckii* subsp. *delbrueckii* LDD01 DSMZ 20074 DSM 22106 in a quantity in weight comprised in the ratio 1:1:1:1 to 3:3:3:1 (for example $1\times10^9$ CFU/strain/dose and $3\times10^9$ CFU/strain/dose) and a quantity of NAC comprised between 50 and 150 mg exerts strong antagonistic action.

In the composition of the present invention, the mixture of strains of bacteria is present in a quantity comprised between 0.5% and 20% by weight, compared with the total weight of the composition, preferably of between 2.5% and 8%.

In a preferred embodiment, the composition can furthermore comprise at least one prebiotic fibre and/or carbohydrates with bifidogenic action. The prebiotic fibre which has an application in the composition of the present invention is a fibre which must be used by the strains of bacteria present in the composition, but not by the pathogens which it is intended to antagonise. In the event that the pathogen to be antagonised belongs to the genus *Candida*, the fructo-oligosaccharides (FOS) and the galacto-oligosaccharides (GOS) have a valid application because said fibres are not used by *Candida*; whereas the gluco-oligosaccharides (GOSα) are capable of directly inhibiting *E. coli* by means of several metabolites. The prebiotic fibre can therefore be chosen, according to the needs of the case and the pathogen to be antagonised, between: inulin, fructo-oligosaccharides (FOS), galacto- and transgalacto-oligosaccharides (GOS and TOS), gluco-oligosaccharides (GOSα), xylo-oligosaccharides (XOS), chitosan-oligosaccharides (COS), soya-oligosaccharides (SOS), isomalto-oligosaccharides (IMOS), resistant starch, pectin, psyllium, arabino-galactanes, gluco-mannanes, galacto-mannanes, xylanes, lactosaccharose, lactulose, lactitol and various other types of rubbers, acacia fibre, carruba fibre, oat fibre, bamboo fibre, fibres from citruses and, in general, fibres containing a soluble portion and an insoluble portion, in variable ratios to each other. In a preferred embodiment of the invention, the composition comprises at least one prebiotic fibre chosen from among those mentioned above and/or suitable mixtures between them in any relative percentage. The quantity of prebiotic fibres and/or of carbohydrates with bifidogenic action, if present in the composition, is comprised between 0% and 60% by weight, preferably between 5% and 45% and even more preferably between 10% and 30%, compared with the total weight of the composition. In this case the composition or supplement has a symbiotic action and functional properties.

Furthermore, the composition can also comprise other active ingredients and/or components such as vitamins, minerals, bioactive peptides, substances with anti-oxidising action, hypocholesterolaemic agent, hypoglycaemic agent, anti-inflammatory and anti-sweetening agents in a quantity generally comprised between 0.001% and 20% by weight, preferably between 0.01% and 5% by weight, in any event depending on the type of active component and its recommended daily dose if any, compared with the total weight of the composition.

The dietary composition which is the subject of the present invention (for example, a symbiotic composition, or a supplement or a pharmaceutical composition) is prepared according to the techniques and the equipment known to experts in the field.

In a preferred embodiment, the composition contains bacteria in a concentration comprised between $1\times10^6$ and $1\times10^{11}$ CFU/g of mixture of bacteria, preferably between $1\times10^8$ and $1\times10^{10}$ CFU/g of mixture of bacteria.

In a preferred embodiment, the composition contains bacteria in a concentration comprised between $1\times10^6$ and $1\times10^{11}$ CFU/dose, preferably between $1\times10^8$ and $1\times10^{10}$ CFU/dose. The dose can be comprised between 0.2 and 10 g, for example it is of 0.25 g, 1 g, 3 g, 5 g or 7 g. The probiotic bacteria used in the present invention can be in solid form, in particular in the form of powder, dehydrated powder or lyophilized form. All the compositions of the present invention are prepared according to techniques known to experts in the field and by the use of known equipment.

In one embodiment, the composition of the present invention comprises furthermore a drug for reducing or treating gastric hyperacidity. This composition is a pharmaceutical composition and forms a subject of the present invention. Said drug is chosen from the group comprising or, alternatively, consisting of: inhibitors of receptor H2, preferably cimetidine, famotidine, nizatidine or ranitidine; prostaglandins preferably misoprostol; protectors of the gastric mucosa, preferably bismuth salts or sucralfate; antimuscarinic or parasympatholytic drugs, preferably pirenzepine or pipenzolate; antacids, preferably sodium bicarbonate, aluminium hydroxide or magnesium hydroxide; proton pump inhibitors, preferably Lansoprazole, Esometazole, Rabeprazole, Pantoprazole and Omeprazole. Preferably, said drug is chosen from the group comprising or, alternatively, consisting of: inhibitors of receptor H2, preferably cimetidine, famotidine, nizatidine or ranitidine; antimuscarinic or parasympatholytic drugs, preferably pirenzepine or pipenzolate; antacids, preferably sodium bicarbonate, aluminium hydroxide, magnesium hydroxide; proton pump inhibitors, preferably chosen from the group comprising Lansoprazole, Esometazole, Rabeprazole, Pantoprazole and Omeprazole.

Even more preferably, said drug is chosen from the group comprising or, alternatively, consisting of: inhibitors of receptor H2, preferably cimetidine, famotidine, nizatidine or ranitidine; proton pump inhibitors, preferably chosen from the group comprising Lansoprazole, Esometazole, Rabeprazole, Pantoprazole and Omeprazole. In a preferred embodiment, the composition of the present invention is a pharmaceutical composition comprising the bacteria described in Table 1 or in Table 2 or in the preferred embodiments listed above, said bacteria being in association with a drug indicated for reducing or treating gastric hyperacidity, as listed above. Advantageously, the drug is a proton pump inhibitor chosen from the group comprising Lansoprazole, Esometazole, Rabeprazole, Pantoprazole and Omeprazole. Both the bacteria and the drug are intimately present in the said composition. For example, the bacteria and the drug are present together in a tablet, a pastille or a granulate in a pharmaceutical form suitable for oral administration.

It is essential that the bacteria and the drug are administered simultaneously and act simultaneously because it is necessary to restore the barrier effect removed by the proton pump inhibitors (PPIs), thanks to the action of the probiotic bacteria of the present invention, which produce bacteriocins and are capable of colonising the stomach as a result of the fact that the proton pump inhibitors have raised the pH to a value of about 4 to 5.5; preferably of 4.5 to 5.

In another preferred embodiment, the composition of the present invention is in the form of a medical device. In this case the bacteria are present in a composition suitable for oral administration such as for example a tablet, a pastille or a granulate and, separately, the drug indicated for reducing or treating gastric hyperacidity, as described above, is present in another composition suitable for oral administration. Advantageously, the drug is a proton pump inhibitor chosen from the group comprising Lansoprazole, Esometazole, Rabeprazole, Pantoprazole and Omeprazole.

Two tablets, for example, are therefore administered, one containing the bacteria and the other containing the drug. In any event the two tablets must be administered simultaneously, given that it is necessary for the bacteria to act simultaneously with the action of the proton pump inhibitors. In the case of the medical device, too, it is essential that the bacteria and the drug are administered at a short distance in time because it is necessary to restore the barrier effect removed by the proton pump inhibitors (PPIs), thanks to the action of the bacteria which produce bacteriocins which are capable of colonising the intestine as a result of the fact that the proton pump inhibitors have raised the pH to a value of about 4 to 5.5; preferably of 4.5 to 5.

The Applicant has found that the bacteria selected and listed in Table 1 or Table 2 or in the preferred embodiments mentioned above, are capable of colonising in the stomach at a pH value of around 5 so as to restore the barrier effect reduced or eliminated by the raising of the pH following the action of the drugs indicated for reducing or treating gastric hyperacidity such as, for example, a proton pump inhibiting drug chosen from the group comprising Lansoprazole, Esometazole, Rabeprazole, Pantoprazole and Omeprazole.

In a preferred embodiment, the composition containing the strains of probiotic bacteria of the present invention, said strains being capable of producing specific bacteriocins, is also a useful adjuvant in treatments directed at the final elimination of *Helicobacter pylori* and avoiding recurrences thereof.

A subject of the present invention, therefore, is constituted by a composition comprising at least one strain of bacteria as recited in Table 1 or in Table 2 or in one of the embodiments mentioned above, for use in the preventive and/or curative treatment of infections, disturbances or illnesses caused by the presence of *Helicobacter pylori*, in particular in the preventive and/or curative treatment of recurrences from infections caused by *Helicobacter pylori*.

In the broadest sense of the term, antibiotics are defined as molecular species produced by an organism and active against the growth of other organisms. In practice, however, antibiotics are generally considered as secondary metabolites active at low concentrations in blocking the growth of micro-organisms. The secondary products of the metabolism such as organic acids, ammonia and oxygenated water are not to be included in the category of antibiotics. Antibiotics are molecules, which may be peptide molecules (penicillin), produced by multi-enzymatic systems and whose biosynthesis is not blocked by protein synthesis inhibitors. Bacteriocins, on the other hand, are products of ribosomal synthesis. Bacteriocins are peptide molecules produced by ribosomal synthesis which can also be associated with lipids or carbohydrates. Although some bacteriocins produced by Gram-positive bacteria (*Lactobacillus, Lactococcus*) have inhibition spectra limited to certain strains belonging to the same species as the producing micro-organism, the majority of them show a broad spectrum of action against various bacterial species, both Gram-positive and Gram-negative. The current classification of the bacteriocins is based both on their chemical nature and on their spectrum of action.

EXPERIMENTAL SECTION

A. Methods

The present pilot clinical study was conducted on 10 subjects, 9 of whom had been taking PPIs for more than a month. The group made up of subjects treated with PPIs was further divided into two subgroups: patients treated with PPIs plus a mixture of strains of selected lactobacilli (3 billion *L. rhamnosus* LR06 DSM 21981, 3 billion *L. plantarum* LP01 LMG P-21021, 3 billion *L. pentosus* LPS01 DSM 21980 and 1 billion *L. delbrueckii* subsp. *delbrueckii* LDD01) for 5-10 days before the endoscopic examination. The biological samples, made up of gastric juice and material from duodenal brushing, were taken during the gastroscopy carried out on the patients who had been fasting for 12-24 hours. The biological materials, conserved in Amies liquid, were subjected to microbiological analyses suitable for evaluating the bacterial load. Non-selective culture medium (LaptG) was used to obtain the total bacterial load, while, to select the heterofermenting lactobacilli, MRS broth medium was used with the addition of the antibiotic vancomicin (2 µg/ml), preparing serial dilutions of the starting sample. The last dilution which was found to be positive to bacterial growth (using optical density) made it possible to deduce the order of magnitude of the load itself.

To verify the presence of the probiotic strains administered, PCR assays were carried out with the following primer sets: RhaII/Prl for *L. rhamnosus*; pREV/pentF for *L. pentosus*; pREV/planF for *L. plantarum* and SS1/DB1 for *L. delbr.* subsp. *delbruckii* LDD01.

B. Results

The results for the total bacterial load demonstrated that the subjects treated with PPIs (PPI group totals: PPIs+"PPIs plus probiotics") show a large number of bacteria, both in the gastric juice and in duodenal brushing, in comparison with the control group (no PPI, no probiotics) which was found to be practically sterile (FIG. 1A). Analysis of the bacterial load of the subjects treated with PPIs plus probiotics revealed a considerable difference between the two groups analysed (1.5 Log; FIG. 1B).

FIG. 1A shows the comparison between subjects chronically treated with PPIs (PPI group totals: PPI+"PPI plus probiotics") and the control group. The data are expressed as an average of the colony-forming units (CFU). FIG. 1B refers to the comparison between subjects chronically treated with PPIs and those treated with "PPI plus probiotics". The data are expressed as an average±S.E.M of the colony-forming units (CFU).

The selection of the heterofermenting lactobacilli, by growth in MRS broth with the addition of the antibiotic vancomicin in serial dilutions, allowed us to demonstrate that the majority of the bacteria found in the subjects treated with "PPI plus probiotics", belonged to the heterofermenting group, as shown in the pie chart reproduced in FIG. 2, in which the area is proportional to the total microbial population.

Analysis using species-specific PCR assay showed the presence of the species *L. rhamnosus, L. plantarum* and *L. delbr.* subsp. *delbrueckii* in all the subjects treated with "PPI plus probiotics", while the species *L. pentosus* was not found (Table 3). Probably this species does not possess the characteristics necessary for its survival in the gastric environment. The positive result for the species *L. plantarum*, shown in a subject treated with PPIs only is probably to be attributed to the subject's dietary habits.

Pilot Study
Materials and Methods
1. The Study

A total of 30 individuals (17 men and 13 women) aged between 19 and 57 years and treated with PPIs were spontaneously enrolled (February-March 2011). Another 10 individuals (4 men and 6 women) aged between 22 and 64 years who did not make use of PPIs (proton pump inhibiting drugs) were enrolled as a control group representative of people with normal gastric acidity. The inclusion criteria for taking part in the study comprised: age between 18 and 70 years, chronic treatment with PPIs for at least 3 to 12 consecutive months (for the first three groups), no other health problem known at the time of enrolment, no pathology requiring treatment with antibiotics; they were informed and gave their consent to taking part in the pilot study. The individuals were also selected on the basis of certain exclusion criteria: age below 30 years, pregnancy in progress or breastfeeding, serious chronic degenerative illnesses, serious cognitive deficits, previous abdominal surgery, diverticulitis, immunodeficiency states, concomitant organic intestinal disease, antibiotic treatment. After informed consent was obtained, the individuals were divided into four groups (A, B, C, and D). Groups A and B included subjects who had undergone long-term treatment with PPIs (of at least 12 consecutive months), while Group C included subjects who had undergone a short treatment with PPIs, from 3 to 12 consecutive months. Finally, Group D included the control individuals who had not been treated with PPIs and with physiological gastric barrier effect. Group A (10 individuals) was the control group for long-term treatment with PPIs and received no treatment. Each subject in Group B (10 individuals) received 10 sachets containing 30 mg each of *L. rhamnosus* LR06 (DSM 21981), *L. pentosus* LPS01 (DSM 21980), and *L. plantarum* LP01 (LMG P-21021) corresponding to $3 \times 10^9$ CFU/strain/sachet, and 10 mg of micro-organism *L. delbrueckii* subsp. *delbrueckii* LDD01 (DSM 22106) equivalent to $1 \times 10^9$ CFU/sachet, 60 mg of N-acetylcysteine (NAC) and 2.34 grams of potato maltodextrin. The total number of vital cells per sachet was 10 billion ($10 \times 10^9$ CFU). Group C (10 individuals) was the study group for short-term treatment with PPIs and received no probiotics. The object of this group was to compare the bacterial growth in Group C compared with Group A, because it was assumed that the bacterial concentration in the gastric lumen and in the duodenal mucosa should be greater in subjects who had undergone long-term treatment with PPIs than in patients who had undergone treatment with PPIs for not longer than 12 months. The individuals in Group B consumed one sachet/day during the main meal, preferably at supper, with the object of allowing the bacteria to remain longer in the stomach lumen and to be distributed homogeneously together with the N-acetylcysteine. The contents of the sachet were dissolved in half a glass of cold water before taking. Administration lasted 10 days. The gastric juice and the material from duodenal brushing were collected during gastroscopy on the subjects after a fast of at least 12 hours from the last time that the probiotics were taken. In this way, no less than half a day had passed since the last time that the probiotics were taken by the individuals. More specifically, the gastroscopy was conducted at time zero ($d_0$) in all the Groups (A, B, C and D) and after 10 days ($d_{10}$); i.e. after the end of taking the probiotics with reference to Group B only. The faecal samples were collected on d0 in all the groups (A, B, C and D) and on d10 for Group B only. The subjects in Groups A, B and C continued the treatment with their specific PPI drugs at the same dose for the entire duration of the pilot study.

2. Collecting the Faecal Samples

The faeces were collected at the beginning of the study ($d_0$) in all the groups (A, B, C and D) and in Group B on $d_{10}$. The faecal samples for the count of the specific groups of bacteria in the intestinal flora (about 10 grams) were collected from the volunteers in sterile plastic containers previously filled with 20 ml of Amies liquid transport medium (BD Italy, Milan, Italy), kept at 4° C. at the volunteer's home and delivered to the laboratory within 24 hours of collection.

3. Quantification of the Total Vital Bacterial Cells and Total *Lactobacillus* and Genomic Analysis of PCR Assays on the Gastric Juice and the Duodenal Brushing Material.

The gastric juice and duodenal brushing material were collected during a gastroscopy carried out on patients who had been fasting for 12-24 hours. The gastroscopies were performed at the Gastroenterology Department of the Ospedale Maggiore della Caríta at Novara. The samples of brushing material (about 1-2 grams) were conserved in sterile plastic containers previously filled with 10 ml of Amies liquid transport medium (BD Italy, Milan, Italy). All the samples were kept at 4° C. and delivered to the laboratory within the 24 hours following their collection.

The samples were analysed as soon as they were received by the laboratory and in any event within 24 hours of collection. The samples were weighed and transferred to a sterile container (Stobag), diluted 1:10 weight/volume with Amies medium, and homogenised with a Stomacher apparatus for 4 minutes at 230 rpm. The samples were subjected to a serial decimal dilution using 1 ml of a saline solution in each dilution ($10^{-2}$, $10^{-3}$, $10^{-4}$, $10^{-5}$, $10^{-6}$, $10^{-7}$ and $10^{-8}$ for the counts of total vital cells and total cells of *Lactobacillus*). The samples were plated on specific agar culture mediums. In Group D, the dilutions from $10^{-1}$ to $10^{-6}$ were plated because the bacterial counts were expected to be significantly lower than those of other groups. The non-selective culture medium LAPTG was used for total vital cells, while the selective count of the total *Lactobacillus* was performed by means of the culture Rogosa Acetate Agar (Oxoid, Milan, Italy). All the plates seeded with lactobacilli were incubated for 48 to 72 hours at 37° C. in anaerobic conditions (GasPak) with an Anaerocult kit (Merck, Darmstadt, Germany), while the plates with LAPTg were incubated in aerobic conditions for 24 to 48 hours at 37° C. The species-specific PCR assay was conducted on an extract of total genomic DNA obtained from the samples of gastric juice processed and from the duodenal brushing material, with the object of verifying and quantifying the presence of the probiotic bacteria administered to the volunteers. In particular, the primers used were as follows: *L. rhamnosus* (Rha/PRI), *L. pentosus* (PENT f/PLAN f/pREV), *L. plantarum* (LFPR/PLAN II), and *L. delbrueckii* subsp. *delbrueckii* (Ldel7/Lac2). The quantification of the total population of bacteria and the total of lactobacilli in the gastric juice and in the duodenal brushing material, and also the species-specific PCR assay, were conducted at the Biolab Research Srl Laboratory at Novara, Italy.

4. Quantification of the Specific Microbe Groups Present in the Faecal Samples.

The samples were examined as soon as they reached the laboratory. The samples were weighed (about 30 grams) and transferred to a sterile container (Stobag), diluted with Amies liquid to obtain a 1:10 weight/volume dilution and were subsequently homogenised in a Stomacher apparatus for 4 minutes at 230 rpm. The samples were then subjected to a serial decimal dilution using a sterile saline solution and 0.1 ml of the appropriate dilution ($10^{-4}$, $10^{-5}$, $10^{-6}$, $10^{-7}$, and $10^{-8}$ for total coliforms, *Escherichia coli* and enterococci; $10^{-1}$, $10^{-2}$, $10^{-3}$, $10^{-4}$, and $10^{-5}$ for the yeasts and moulds). The samples were plated on agar culture mediums. The Enterococci were counted using Slanetz-Bartley (SB) agar (Oxoid, Milan, Italy); total coliforms and *Escherichia coli* were counted on Petrifilm CC (3M, Segrate, Milan, Italy) and on Chromo IDCPS (BioMerieux, Florence, Italy), the total yeasts and the moulds on Yeast Extract Dextrose Chloramphenicol (YGC) agar (Sigma-Aldrech, Milan, Italy). The Enterococci, the total coliforms and the *Escherichia coli* were incubated in aerobic conditions at 37° C. for 24 to 48 hours, while the yeasts and moulds were incubated in aerobic conditions at 25° C. for 24 to 48 hours.

Quantification of the microbial groups listed above in the faecal samples was executed at the Biolab Research Srl Laboratory in Novara, Italy.

5. Statistical Analysis

All the values obtained on the concentration of the total bacterial population and on total lactobacilli in the gastric juice and in the duodenal brushing material are expressed as the average of the number of vital cells per ml or per gram of sample±the average standard error (m±SEM). All the values relating to the concentration of specific faecal microbial groups are expressed as the average number of vital cells/gram of faeces±standard error of the average (m±SEM). The paired or independent t-tests of the statistical analyses were used to evaluate the results and compare them between $d_0$ and $d_{10}$ in group B (paired) and $d_0$ between the various groups (independent). In particular, the results of Group A were compared with Groups B, C, and D at $d_0$ (baseline). The differences were considered significant with $p \leq 0.05$.

6. Results 6.1 Quantification of the Total Bacterial Cells, the Total *Lactobacillus* and Genomic Analysis of PCR Assays on the Gastric Juice and the Duodenal Brushing Material.

All the 40 individuals were subjected to gastroscopy at time zero ($d_0$), while Group B was also subjected to gastroscopy at the end of supplementation with probiotics ($d_{10}$). No withdrawals were recorded, as the preparation had been very well tolerated and accepted by each participant in Group B, the only one which received probiotic supplements between $d_0$ and $d_{10}$.

The results regarding the total bacterial cells and the total *Lactobacillus* in the gastric juices and in the duodenal brushing material are shown in Table 4.

TABLE (4)

Quantification of the total bacterial cells and of the total *Lactobacillus* (value ± SEM, $\log_{10}$ CFU/ml of the gastric juice or gram of duodenal brushing material) at $d_0$ (all groups) and at $d_{10}$ (Group B).

| | a) comparison between the four groups at $d_0$ | | | | | | | |
| --- | --- | --- | --- | --- | --- | --- | --- | --- |
| Parameters considered | Group A log CFU/ ml o g | Group B log CFU/ ml o g | Group C log CFU/ ml o g | GroupD log CFU/ ml o g | p (A vs. B) | p (A vs. C) | p (A vs. D) | p (C vs. D) |
| $d_0$ Gastric juice | | | | | | | | |
| Total bacteria | 8.50 ± 0.28 | 8.60 ± 0.17 | 5.47 ± 0.30 | 2.48 ± 0.21 | 0.4441 | 0.0012 | 0.0011 | 0.0910 |
| Total *lactobacillus* | 6.99 ± 0.34 | 7.15 ± 0.25 | 5.01 ± 0.40 | 1.62 ± 0.17 | 0.5767 | 0.1402 | 0.1365 | 0.2822 |

TABLE (4)-continued

Quantification of the total bacterial cells and of the total *Lactobacillus* (value ± SEM, $\log_{10}$ CFU/ml of the gastric juice or gram of duodenal brushing material) at $d_0$ (all groups) and at $d_{10}$ (Group B).

Duodenal brushing

| | | | | | | | | |
|---|---|---|---|---|---|---|---|---|
| Total bacteria | 8.37 ± 0.28 | 8.32 ± 0.33 | 5.80 ± 0.33 | 2.60 ± 0.20 | 0.8204 | 0.0139 | 0.0137 | 0.0739 |
| Total *lactobacillus* | 6.80 ± 0.23 | 6.76 ± 0.33 | 4.00 ± 0.17 | 1.35 ± 0.15 | 0.8868 | 0.0083 | 0.0083 | 0.1387 | b) percentage of total *lactobacillus* at $d_0$ in the four groups

| Biological sample | Group A % | Group B % | Group C % | Group D % |
|---|---|---|---|---|
| Gastric juice | 3.06 | 3.51 | 34.91 | 13.93 |
| Duodenal brushing | 2.71 | 2.74 | 1.58 | 5.59 | c) comparison between time zero ($d_0$) and $d_{10}$ in Group B

| | Group B | | |
|---|---|---|---|
| Time | log CFU/ml or log CFU/g | % of total *Lactobacillus* | p§ |
| $d_0$ | | | |
| Gastric juice | | | |
| Total bacteria | 8.60 ± 0.17 | | ** |
| Total *Lactobacillus* | 7.15 ± 0.25 | 3.51 | ** |
| Duodenal brushing | | | |
| Total bacteria | 8.32 ± 0.33 | | ** |
| Total *Lactobacillus* | 6.76 ± 0.33 | 2.74 | ** |
| $d_{10}$ | | | |
| Gastric juice | | | |
| Total bacteria | 7.71 ± 0.27 | | 0.0023 |
| Total *Lactobacillus* | 7.70 ± 0.27 | 98.03 | 0.0742 |
| Duodenal brushing | | | |
| Total bacteria | 7.47 ± 0.32 | | 0.0256 |
| Total *Lactobacillus* | 7.44 ± 0.32 | 93.50 | 0.0355 |

\*\* Comparison reference time zero ($d_0$)
§Comparison between ($d_0$) and ($d_{10}$)

It is interesting to note that a significant reduction in the total bacterial parameters is present at $d_{10}$ in Group B in comparison with the baseline (Table 1c).

6.2 Results of the Species-Specific PCR Assay

The results of the species-specific PCR assay in Group B at $d_{10}$ compared with $d_0$ further confirmed the presence of the four species of probiotics administered. A general panorama is shown in Table 5.

TABLE 5

Results of the species-specific PCR assay in Group B at $d_0$ and at $d_{10}$. The presence of correlated species is shown by a "+", while their absence is shown by a "−".

| Group | Individuals | *L. plantarum* | *L. rhamnosus* | *L. pentosus* | *L. delbrueckii* subsp *delbrueckii* |
|---|---|---|---|---|---|
| a) gastric juice | | | | | |
| $d_0$ | 1 | + | − | − | − |
| | 2 | − | − | − | − |
| | 3 | − | − | − | − |
| | 4 | − | − | − | − |
| | 5 | − | − | − | − |
| | 6 | − | − | − | − |
| | 7 | − | − | − | − |
| | 8 | − | + | − | − |
| | 9 | − | − | − | − |
| | 10 | − | − | − | − |
| $d_{10}$ | 1 | + | + | − | + |
| | 2 | + | + | − | + |
| | 3 | + | + | + | − |
| | 4 | + | + | − | + |
| | 5 | + | + | + | + |
| | 6 | + | − | − | + |
| | 7 | + | + | − | + |
| | 8 | + | + | + | + |
| | 9 | + | + | − | + |
| | 10 | + | − | + | + |
| b) duodenal brushing | | | | | |
| $d_0$ | 1 | + | − | − | − |
| | 2 | − | − | − | − |
| | 3 | − | − | + | − |
| | 4 | − | − | − | − |
| | 5 | + | − | − | − |
| | 6 | − | − | − | − |
| | 7 | − | − | − | − |

TABLE 5-continued

Results of the species-specific PCR assay in Group B at $d_0$ and at $d_{10}$.
The presence of correlated species is shown by a "+",
while their absence is shown by a "−".

| Group | Individuals | L. plantarum | L. rhamnosus | L. pentosus | L. delbrueckii subsp delbrueckii |
|---|---|---|---|---|---|
| | 8 | − | − | − | − |
| | 9 | − | − | − | − |
| | 10 | − | − | − | − |
| $d_{10}$ | 1 | + | + | + | + |
| | 2 | + | + | − | + |
| | 3 | − | + | + | − |
| | 4 | + | + | − | + |
| | 5 | + | + | − | + |
| | 6 | + | + | − | + |
| | 7 | + | + | − | + |
| | 8 | + | + | + | + |
| | 9 | + | + | + | − |
| | 10 | + | + | + | + |

In the gastric juice, *L. plantarum* and *L. delbrueckii* subsp. *delbrueckii* were the two most representative species since 10 and 9 individuals, respectively, out of a total of 10 individuals were positive compared with 1 and 0 at the baseline ($d_0$). In the duodenal brushing, *L. plantarum* and *L. rhamnosus* were present in 9 and 10 subjects, respectively, out of a total of 10 subjects compared with 2 and 0 at the baseline ($d_0$).

6.3 Count of the Specific Microbe Groups in the Faecal Samples.

The results on total *Enterococcus*, total coliforms, *Escherichia coli*, yeasts and moulds in the faecal samples are shown in Table 6.

TABLE 6

Quantification of the specific microbial groups in faecal samples at $d_0$ (all groups) and $d_{10}$
(Group B). The results are expressed as $\log_{10}$ of CFU/grams of faeces (value ± SEM).

a) comparison between the four groups at $d_0$

| Parameters considered | Group A $\log_{10}$ CFU/g | Group B $\log_{10}$ CFU/g | Group C $\log_{10}$ CFU/g | Group D $\log_{10}$ CFU/g | p (A vs. B) | p (A vs. C) | p (A vs. D) | p (C vs. D) |
|---|---|---|---|---|---|---|---|---|
| $d_0$ | | | | | | | | |
| *Enterococcus* spp | 7.68 ± 0.17 | 7.80 ± 0.25 | 7.38 ± 0.27 | 6.39 ± 0.17 | 0.5185 | 0.1062 | 0.0021 | 0.0479 |
| Total coliforms | 9.59 ± 0.17 | 9.55 ± 0.16 | 9.39 ± 0.27 | 8.75 ± 0.14 | 0.8019 | 0.2946 | 0.0147 | 0.0338 |
| *Escherichia coli* | 9.52 ± 0.17 | 9.44 ± 0.18 | 9.33 ± 0.28 | 8.72 ± 0.14 | 0.6818 | 0.3550 | 0.0227 | 0.0444 |
| Yeasts | 6.07 ± 0.17 | 5.95 ± 0.14 | 5.30 ± 0.26 | 2.22 ± 0.19 | 0.5733 | 0.0486 | 0.0223 | 0.0051 |
| Moulds | 5.60 ± 0.14 | 5.64 ± 0.14 | 4.83 ± 0.24 | 1.90 ± 0.17 | 0.8106 | 0.0078 | 0.0027 | 0.0187 | b) percentage of total coliforms which consist of *Escherichia coli* at $d_0$ in the four groups and at $d_{10}$ in Group B

| Time | Group A % | Group B % | Group C % | Group D % |
|---|---|---|---|---|
| $d_0$ | | | | |
| *Escherichia coli* | 83.87 | 77.43 | 86.51 | 92.63 |
| $d_{10}$ | | | | |
| *Escherichia coli* | / | 91.12 | / | / | c) comparison between the baseline ($d_0$) and $d_{10}$ in Group B.

| | Group B | |
|---|---|---|
| Time | $\log_{10}$ CFU/g | p§ |
| $d_0$ | | |
| *Enterococcus* spp | 7.80 ± 0.25 | ** |
| Total coliforms | 9.55 ± 0.16 | ** |
| *Escherichia coli* | 9.44 ± 0.18 | ** |
| Yeasts | 5.95 ± 0.14 | ** |
| Moulds | 5.64 ± 0.14 | ** |
| $d_{10}$ | | |
| *Enterococcus* spp | 6.99 ± 0.23 | 0.0155 |
| Total coliforms | 8.01 ± 0.24 | 0.0064 |
| *Escherichia coli* | 7.97 ± 0.23 | 0.0105 |

TABLE 6-continued

Quantification of the specific microbial groups in faecal samples at $d_0$ (all groups) and $d_{10}$
(Group B). The results are expressed as $\log_{10}$ of CFU/grams of faeces (value ± SEM).

| Yeasts | 3.56 ± 0.18 | 0.0066 |
| Moulds | 4.30 ± 0.15 | 0.0053 |

** Comparison reference at time zero $d_0$
§Comparison between $d_0$ and $d_{10}$ in Group B Results The study confirmed a significant bacterial growth in the upper gastro-intestinal tract in subjects who had been taking PPIs for more than 12 consecutive months (p=0.0011 and p=0.0137 for total bacteria in the gastric juice and in the duodenal brushing material, respectively, in Group A versus Group D which represents the general population; similar statistical results were found from the comparison off Group B and Group D in the same way). Comparison between groups A and C (subjects treated with PPIs for a period of from 3 to 12 months) demonstrated statistical significance in 3 out of 4 parameters. In this way, the duration of the PPI treatment is a factor which can determine the degree of bacterial proliferation in the upper gastrointestinal tract. The individuals treated in the short term seem to be more similar to the general population rather than to subjects who had undertaken long-term treatment with PPIs.

An interesting aspect refers to the higher percentage of total *Lactobacillus* in the gastric juice of subjects treated in the short term (34.91%, 5.01 $\log_{10}$ CFU/ml in Group C) compared with subjects treated long-term (3.06%, 6.99 $\log_{10}$ CFU/ml in Group A; 3.51%, 7.15 $\log_{10}$ CFU/ml in Group B). This higher concentration, however, does not reflect the results of the duodenal brushing (1.58%, 4.00 $\log_{10}$ CFU/ml in Group C).

The administration of the 4 strains of bacteria listed above, i.e. *L. rhamnosus* LR06, *L. pentosus* LPS01, *L. plantarum* LP01 and *L. delbrueckii* subsp. *delbrueckii* LDD01, including 60 mg of NAC for 10 days was sufficient to significantly change the typical bacterial growth in the subjects treated with PPIs for more than 12 months, so as to restore a protective barrier against possible pathogens of dietary origin (p=0.0023 and p=0.0256 for the total of bacteria in the gastric juice and the duodenal brushing material, respectively, in Group B at $d_{10}$ compared with $d_0$, Table 4c.

Another interesting result was the percentage of total bacteria represented by lactobacilli in the various groups. In control subjects who were not taking PPIs, the bacteria belonging to the genus *Lactobacillus* represent about 14% of the total of the gastric microflora, while in patients treated with PPIs for more than 12 months, lactobacilli represented only about 3% of the total bacteria, suggesting therefore that the great majority of the gastric micro-organisms were composed of other, potentially harmful, microbial groups. At the end of the period of supplementation by probiotics ($d_{10}$) in Group B, lactobacilli constituted 98% of the total bacteria in the gastric juice, and an increase in their concentration compared with time zero was recorded, although it is not statistically significant (p=0.074). The lack of statistical significance could be explained in the light of the significant parallel reduction in total gastric bacteria (7.71 $\log_{10}$ CFU/ml compared with 8.60 log 10 CFU/ml, p=0.0023). On the other hand, the percentage of *Lactobacillus* in the duodenal brushing material was significantly higher at $d_{10}$ compared with the baseline (p=0.0355).

The results of the species-specific PCR assay, furthermore, confirmed the capacity of the probiotics administered together with NAC to effectively colonise the gastric lumen and the duodenal mucosa in the subjects treated with PPIs for more than 12 consecutive months (Tables 5a and 5b). This aspect may help to inhibit and replace the possibly harmful pathogens bacteria or indeed those which are commonly present in subjects treated long-term with PPIs. This datum is more significant if it is considered that the gastroscopies were all executed at least 12 hours after the last time that probiotics had been taken, thus demonstrating the capacity of these beneficial bacteria to persist significantly in the stomach and on the surface of the duodenal mucosa. NAC was used for its mechanical effects against bacterial biofilms, in order to prevent a possible new formation of biofilms in subjects undergoing long-term treatment with PPIs.

The results of the faecal samples demonstrated, on the one hand, a significant increase in all the microbial parameters taken into consideration in the individuals treated with PPIs for a period of at least 12 months (comparison between Groups A and D): p=0.0021, p=0.0147, p=0.0227, p=0.0223 and p=0.0027 for *Enterococcus* spp., total coliforms, *E. coli*, yeasts and moulds, respectively). In any case, a short-term administration of PPIs, from 3 to 12 months, was sufficient to induce a significant faecal increase in all the five parameters, although the statistical significance was lower (see data for Group C compared with D: p=0.0479, p=0.0338, p=0.0444, p=0.0051, and p=0.0187, respectively) (Table 6). On the other hand, the statistical comparison between the subjects PPI treated long-term and short-term was significant only for the yeasts and moulds (p=0.0486 and p=0.0078, respectively), thus suggesting that for *Enterococcus* spp. and for Gram-negative bacteria, taking minimal quantities of PPIs for three months is sufficient to mediate the majority of the increase observed after 12 months of treatment. Yeasts and moulds very probably need more time to colonise the intestinal flora after the alteration of the gastric barrier, since a significant additional increase was recorded in long-term subjects compared with short-term subjects (Group A compared with Group C).

The total coliforms usually represent about 1% of the total population of human faecal bacteria in concentrations of around $10^9$ bacteria per gram (37). Another interesting result is the percentage of total coliforms constituted by *Escherichia coli*. It is known, in fact, that this bacterium represents the majority of the total population of coliforms in the human intestine, generally amounting to 93-94% (38). The total coliform bacteria present in the human intestine are made up of four genera of the family of the Enterobacteriaceae, in particular *Escherichia, Klebsiella, Enterobacter* and *Citrobacter*, with *Klebsiella* normally amounting to about 1% and *Enterobacter/Citrobacter* spp. representing together about 6%. The results for Group D substantially confirmed this evidence, since 92.6% of total coliforms was made up of *E. coli*. In the subjects who had undergone long-term treatment with PPIs, however, this percentage was reduced to 83.9% (Group A) and to 77.4% (Group B), thus suggesting an abnormal excessive growth of the genera *Klebsiella* and/or *Enterobacter/Citrobacter* in the intestine as a consequence of the destruction of the gastric barrier. This increase could be considered harmful since some species such as *Klebsiella pneumoniae, Klebsiella oxytoca* and *Enterobacter cloacae* could exert significant pathogenic action on the host, ranging from hospital infections of the blood (BSI) through to acute appendicitis and antibiotic-associated haemorrhagic colitis (AAHC).

The *Enterococcus* spp. are normally present in human faeces in concentrations from $10^5$ to $10^7$ bacteria per gram. The data obtained on the control population confirmed this evidence, as 6.39 $\log_{10}$ CFU/ml were counted in the faecal samples. Long-term treatment with PPIs caused a significant increase in this microbial genus in the human intestine (7.68 $\log_{10}$ CFU/ml in Group A and 7.80 $\log_{10}$ CFU/ml in Group B).

The most important question represented by *Enterococcus* spp., in particular by *Enterococcus faecium*, is their intrinsic antibiotic resistance, specially towards penicillin and vancomicin. The enterococci are the third most common cause of infective endocarditis, and the effect of tolerance to penicillin on therapeutic results has been evident since the end of the 1940s. In any case, epidemiological studies have demonstrated that the strains of *E. faecium* associated with nosocomial infections, including endocarditis, are types of sequences different from the commensal strains which colonise the gastrointestinal tract of healthy human beings, even though the possibility cannot be excluded that some harmful biotypes may have colonised the human bacterial flora of the subjects treated with PPIs.

The complex analyses of the faeces at baseline time confirmed the weakening or indeed the complete interruption of the gastric barrier effect, since the composition of the intestinal flora showed that it is profoundly modified in persons who take PPIs for at least three months. Gram-negative bacteria, such as total coliforms and *Escherichia coli*, were significantly higher than in the controls, while yeasts and moulds increased by about 4 $\log_{10}$. Faecal Enterococci were up by more than 1 $\log_{10}$. It is also interesting to note the correlation between the duration of taking PPIs and the size of the faecal increases in the five microbial groups analysed, chosen as evidence of a potential dysmicrobism.

The four probiotics studied in association with NAC were able to reduce all the faecal parameters (p=0.0155, p=0.0064, p=0.0105, p=0.0066, and p=0.0053 for *Enterococcus* spp., total coliforms, *E. coli*, yeasts and moulds, respectively, at $d_{10}$ compared with the baseline value). In particular, the reduction in total coliforms, *E. coli*, yeasts and moulds was more than one log 10 after 10 days of supplementation with the probiotics. At the end of the supplementation with the probiotics in Group B, total coliforms and concentrations of *E. coli* were significantly lower than values found in the general population (Group D) (p=0.0182 and p=0.0229, respectively), thus confirming the considerable antagonistic action of the probiotic bacteria against *Escherichia coli*.

In conclusion, the administration of an association of specific strains of *L. rhamnosus* LR06, *L. pentosus* LPS01, *L. plantarum* LP01, and *L. delbrueckii* subsp. *delbrueckii* LDD01, including also an efficacious quantity of N-acetylcysteine, is capable of significantly reducing bacterial proliferation at the level of the stomach and duodenum, reducing Gram-negative bacteria, *Enterococcus* spp., yeasts and moulds in the intestinal flora after 10 days of oral supplementation, thus rapidly rebalancing its composition and restoring a protective barrier against harmful bacteria, especially at stomach level.

N-acetylcysteine (NAC) was used because of its capacity to mechanically prevent the possible formation of a bacterial biofilm, and showed itself to be effective since the concentration of the various bacteria other than lactobacilli both in the gastric juice and in the samples from brushing the duodenum was significantly reduced.

All the probiotic strains used in this study have previously demonstrated a significant antagonistic action in vitro on specific strains of *Escherichia coli*, among them the enterohaemorrhagic serotype 0157:H7, and could therefore be used to effectively prevent infections mediated by these harmful or pathogenic microbes.

In the light of an actually more widespread use of PPIs, concomitant oral supplementation with probiotics and NAC as used in this pilot study represents an innovative strategy capable of restoring, at least partially, a normal gastric barrier effect; thus reducing the threat of gastrointestinal infections of dietary origin in a large part of the population with reduced intragastric acidity.

TABLE 3

| Volunteers | | *L. plantarum* | *L. rhamnosus* | *L. pentosus* | *L. delbr.* subsp. *delbrueckii* |
|---|---|---|---|---|---|
| PPI | 2 | + | − | − | − |
| | 3 | − | − | − | − |
| | 10 | − | − | − | − |
| PPI plus probiotics | 1 | + | + | − | + |
| | 5 | + | + | − | + |
| | 6 | + | + | − | + |
| | 7 | + | + | − | + |
| | 8 | + | − | − | − |
| | 9 | + | + | − | + |

The invention claimed is:

1. A method of treating a subject who is taking drugs to reduce or treat gastric hyperacidity, the method comprising administering to the subject a pharmaceutical or dietary composition or a supplement or a medical device comprising an effective amount of a mixture of *Lactobacillus pentosus* LPS01 DSM 21980, *Lactobacillus plantarum* LP01 LMG P-21021, *Lactobacillus rhamnosus* LR06 DSM 21981, and *Lactobacillus delbrueckii* subsp. *delbrueckii* LDD01 (DSMZ 20074) DSM 22106 in association with N-acetylcysteine,
said strains being capable of colonizing the stomach at a pH value comprised between 4.0 and 5.5 and of producing bacteriocins and/or metabolites and/or oxygenated water.

2. The method according to claim 1, wherein the pharmaceutical or dietary composition or a supplement or a medical device further comprises
*Lactobacillus fermentum* LF 09 DSM 18298 and/or *Lactococcus lactis* NS 01 DSM 19072;
or at least one strain chosen from the group consisting of:
*Lactobacillus reuteri* LRE 01 DSM 23877;
*Lactobacillus reuteri* LRE 02 DSM 23878;
*Lactobacillus reuteri* LRE 03 DSM 23879; and
*Lactobacillus reuteri* LRE 04 DSM 23880.

3. The method according to claim 1, wherein the drugs are to for reducing or treating dyspepsia, gastroduodenal ulcer, gastric ulcer, peptic ulcer, duodenal ulcer, gastritis caused by *Helicobacter pylori* and gastroesophageal reflux disease in the subject.

4. The method according to claim 3, wherein the pharmaceutical or dietary composition or supplement or medical device further comprises a drug belonging to the category of proton pump inhibitors (PPI).

5. The method according to claim 4, wherein the mixture of bacteria and said drug are formulated together in a pharmaceutical form for oral use.

6. The method according to claim 1 wherein the mixture of bacteria is in an effective amount for inhibition and/or curative treatment of infections, disturbances or illnesses caused by the presence of *Helicobacter pylori*, preferably in the inhibition and/or curative treatment of recurrences from infections caused by *Helicobacter pylori*.

7. The method according to claim 1, wherein the pharmaceutical or dietary composition or a supplement or a medical device comprises each strain of bacteria in a quantity comprised between $1 \times 10^9$ and $10 \times 10^9$ CFU/strain/dose.

8. The method according to claim 1, wherein the N-acetylcysteine is in a quantity comprised between 10 and 200 mg.

* * * * *